US012740785B2

(12) United States Patent
Billon

(10) Patent No.: US 12,740,785 B2
(45) Date of Patent: Sep. 22, 2026

(54) COVER DEVICE FOR A SURGICAL SITE, CARTRIDGE FOR A SURGICAL STAPLER, AND RELATED SURGICAL METHODS

(71) Applicant: Andrew Billon, Indiana, PA (US)

(72) Inventor: Andrew Billon, Indiana, PA (US)

(73) Assignee: Evergreen Surgical Solutions, LLC, Indiana, PA (US)

( * ) Notice: Subject to any disclaimer, the term of this patent is extended or adjusted under 35 U.S.C. 154(b) by 0 days.

(21) Appl. No.: 18/792,947

(22) Filed: Aug. 2, 2024

(65) Prior Publication Data

US 2025/0040933 A1 Feb. 6, 2025

Related U.S. Application Data

(60) Provisional application No. 63/517,474, filed on Aug. 3, 2023.

(51) Int. Cl.

*A61B 17/115* (2006.01)
*A61B 17/11* (2006.01)

(Continued)

(52) U.S. Cl.

CPC ......... *A61B 17/115* (2013.01); *A61B 17/1114* (2013.01); *A61B 17/1155* (2013.01);

(Continued)

(58) Field of Classification Search

CPC ................ A61B 17/068; A61B 17/072; A61B 17/07207; A61B 17/07292; A61B 17/115; A61B 17/1155; A61B 17/00234; A61B 31/08; A61B 31/146; A61B 31/16; A61L 27/36; A61L 27/3604; A61F 2/02; A61F 2/08; A61F 2/0063

(Continued)

(56) References Cited

U.S. PATENT DOCUMENTS 8,167,895 B2 * 5/2012 D'Agostino ......... A61B 17/072 606/151
8,453,908 B2 6/2013 Bedi et al.

(Continued)

OTHER PUBLICATIONS

Hensler Surgical, "Amniotic & Allogenic Graft", 2019, pp. 1-10, Distributed by Hensler Surgical Products, LLC.

(Continued)

*Primary Examiner* — Anna K Kinsaul
(74) *Attorney, Agent, or Firm* — The Webb Law Firm

(57) ABSTRACT

A cartridge configured to be connected to a surgical stapler includes an anvil leg having an inwardly facing surface and a staple leg pivotally connected to the anvil leg. The staple leg includes a plurality of staples and an inwardly facing surface configured to move towards the inwardly facing surface of the anvil leg. The inwardly facing surface of the staple leg includes a plurality of openings positioned for the plurality of staples to pass through the plurality of openings to tissue positioned between the anvil leg and the staple leg. The cartridge also includes a cover device having at least one sheet of amnion attached to the inner surface of at least one of the anvil leg or the staple leg configured to attach to the tissue positioned between the inwardly facing surface of the anvil leg and the inwardly facing surface of the staple leg.

14 Claims, 18 Drawing Sheets

(51) Int. Cl.
*A61L 31/00* (2006.01)
*A61L 31/16* (2006.01)

(52) U.S. Cl.
CPC ............. *A61L 31/005* (2013.01); *A61L 31/16* (2013.01); *A61B 2017/1132* (2013.01); *A61B 2017/1139* (2013.01)

(58) Field of Classification Search
USPC ..... 227/19, 175.1, 176.1, 180.1; 606/1, 139, 606/151, 219
See application file for complete search history.

(56) References Cited

U.S. PATENT DOCUMENTS 8,657,176 B2 * 2/2014 Shelton, IV ..... A61B 17/00234 227/19
9,005,243 B2 * 4/2015 Stopek ............. A61B 17/07292 227/175.1
9,010,612 B2 * 4/2015 Stevenson .......... A61B 17/1155 227/176.1
9,597,082 B2 3/2017 Stokes et al.
9,775,618 B2 * 10/2017 Bettuchi ............ A61B 17/1155
10,154,840 B2 * 12/2018 Viola ............... A61B 17/00491
10,357,249 B2 * 7/2019 Carter .................. A61B 17/105
10,390,827 B2 * 8/2019 Hodgkinson .... A61B 17/07292
10,499,913 B2 * 12/2019 Vendely .................... A61F 2/04
10,918,388 B2 2/2021 Nativ et al.
2010/0012703 A1 * 1/2010 Calabrese ............ A61B 17/068 227/176.1
2012/0010727 A1 1/2012 Young et al.
2013/0238100 A1 9/2013 Young
2016/0000968 A1 1/2016 Koob et al.
2017/0055986 A1 * 3/2017 Harris ................... A61M 37/00
2019/0254671 A1 * 8/2019 Shankarsetty ... A61B 17/07292
2021/0228331 A1 * 7/2021 Scarpone .............. A61F 2/0811
2022/0133955 A1 5/2022 McQueen et al.

OTHER PUBLICATIONS

Sripathi et al., "Factors Contributing to Anastomotic Leakage Following Colorectal Surgery: Why, When, and Who Leaks", 2022, Cureus, vol. 14:10, pp. 1-11.

* cited by examiner

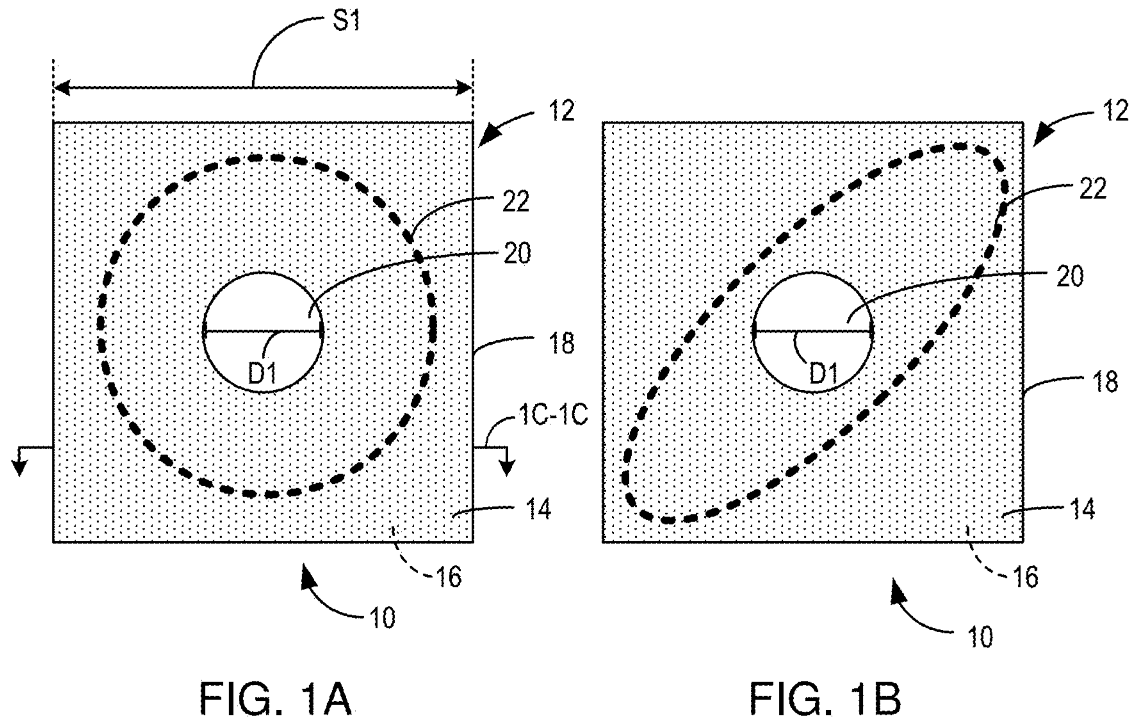
FIG. 1A
FIG. 1B
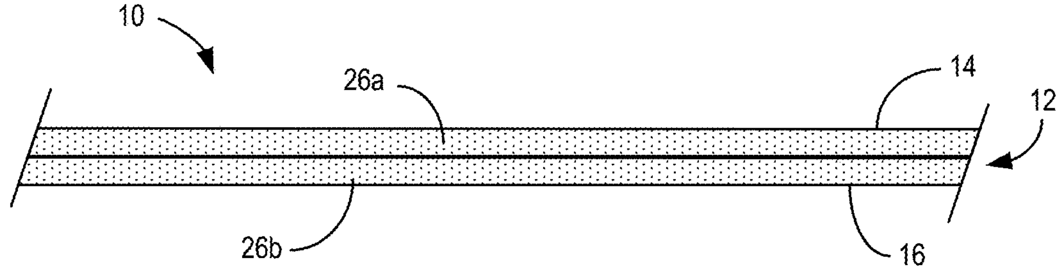
FIG. 1C 710
712
718
722
W3
714
724
716
L3
L3
718

710
718
712
722
714
716
724
720
718

710
720
T3
722
W3

710
718
712
722
716
714
122,126
724
718

COVER DEVICE FOR A SURGICAL SITE, CARTRIDGE FOR A SURGICAL STAPLER, AND RELATED SURGICAL METHODS

CROSS REFERENCE TO RELATED APPLICATION

This application claims the benefit of U.S. Provisional Patent Application No. 63/517,474, filed Aug. 3, 2023, entitled "Cover Device for a Surgical Site, Cartridge for Surgical Stapler, and Related Surgical Methods," the disclosure of which is hereby incorporated by reference in its entirety.

BACKGROUND OF THE INVENTION

Gastrointestinal (GI) or intestinal anastomosis (e.g., bowl anastomosis) is a common surgical technique used following damage or resection of GI sections, such as sections of the small or large intestines, or attachment of one portion of the GI tract to another, such as a sigmoid to rectal anastomosis. Two common surgical methods are side-to-side anastomosis (SSA) and end-to-end anastomosis (EEA). In both surgical methods, a connection is formed between a lumen of an open end of the GI tract and a lumen of another end of the GI tract.

Anastomosis procedures are often performed using a surgical stapler for deploying multiple staples for connecting a first tissue section to a second tissue section during the anastomosis procedure. Many different designs of surgical staplers are currently available including circular surgical staplers and staplers including elongated legs that provide linear or elongated staple regions in tissue. Surgical staplers can be manually operated by a surgeon and/or controlled by robotic-assisted surgery systems.

However, currently available surgical stapler devices and surgical methods are susceptible to complications and failures, which can include leakage, inflammation, and rupture. In particular, anastomotic leaks, which have an incidence of up to 20%, can lead to significant morbidity, such as peritonitis, abscess formation, sepsis and death. See Sripathi S, Khan MI, Patel N, Meda RT, Nuguru SP, Rachakonda S. *Factors contributing to anastomotic leakage following colorectal surgery: Why, when and who leaks? Cureus.* 2022 October; 10: e29964.

In view of such complications, there is a need in the art for medical devices and surgical methods that provide more secure connections, without leaks, between tissue sections in anastomosis surgical procedures. The surgical devices and methods disclosed herein are provided to address these complications.

SUMMARY OF THE INVENTION

According to an aspect of the disclosure, a cartridge configured to be connected to a surgical stapler includes an anvil leg having an inwardly facing surface and a staple leg pivotally connected to the anvil leg. The staple leg includes a plurality of staples positioned in an interior of the staple leg and an inwardly facing surface configured to move towards the inwardly facing surface of the anvil leg. The inwardly facing surface of the staple leg includes a plurality of openings positioned for the plurality of staples to pass through the plurality of openings to tissue positioned between the inwardly facing surface of the anvil leg and the inwardly facing surface of the staple leg. The cartridge also includes a cover device having at least one sheet of amnion attached to the inner surface of at least one of the anvil leg or the staple leg configured to attach to the tissue positioned between the inwardly facing surface of the anvil leg and the inwardly facing surface of the staple leg.

According to another aspect of the disclosure, a cover device configured to be positioned on a leg of a surgical stapler and to transfer from the leg of the surgical stapler to tissue at a surgical site during a stapling procedure includes a removable backing and at least one sheet of amnion attached to and in surface-to-surface contact with the removable backing. The at least one sheet is configured to be attached to an inwardly facing surface of the leg of the surgical stapler and, once the backing is removed from the at least one sheet, to transfer from the leg to the tissue at the surgical site.

According to another aspect of the disclosure, an assembly method for a surgical stapler includes a step of applying at least one sheet with amnion to an inwardly facing surface of a leg of a stapler cartridge by pressing a surface of the at least one sheet against the inwardly facing surface of the leg of the surgical stapler. The method also includes removing a removable backing attached to the at least one sheet, thereby exposing an inwardly facing surface of the at least one sheet so that the at least one sheet can be attached to tissue of a patient during a stapling surgical procedure.

According to another aspect of the disclosure, a method for performing a surgical procedure includes a step of preparing a surgical stapler having a cartridge for the surgical procedure. The cartridge includes an anvil leg having an inwardly facing surface and a staple leg pivotally connected to the anvil leg. The staple leg includes a plurality of staples positioned in an interior of the staple leg and an inwardly facing surface configured to move towards the inwardly facing surface of the anvil leg. The inwardly facing surface of the staple leg includes a plurality of openings positioned for the plurality of staples to pass through the plurality of openings. The cartridge also includes a cover device having at least one sheet with amnion attached to the inner surface of at least one of the anvil leg or the staple leg. The method further includes steps of: positioning patient tissue of a surgical site between the anvil leg and the staple leg of the cartridge; tightening the cartridge causing the staple leg to move toward the anvil leg and causing the at least one sheet to press against the patient tissue; and activating the surgical stapler causing the plurality of staples to pass from the staple leg through the patient tissue and the at least one sheet, thereby forming a staple line in the patient tissue.

According to another aspect of the disclosure, an implantable surgical cover device configured to be implanted over tissue of a patient at a surgical site during a surgical stapling procedure includes: at least one sheet with at least one layer of amnion. The at least one sheet includes a first surface, a second surface, and a peripheral edge extending between the first surface and the second surface. The cover device also includes at least one opening extending through the at least one sheet provided to guide a user for proper positioning of the surgical stapler during the surgical procedure and one or more markings printed or embossed on the at least one sheet showing proper positioning for a staple line provided by the surgical stapler.

Other non-limiting examples of the present disclosure are set forth in the following illustrative numbered clauses:

Clause 1: A cartridge configured to be connected to a surgical stapler, comprising an anvil leg comprising an inwardly facing surface; a staple leg pivotally connected to the anvil leg comprising a plurality of staples positioned in an interior of the staple leg and an inwardly facing surface configured to move towards the inwardly facing surface of the anvil leg, the inwardly facing surface comprising a plurality of openings positioned for the plurality of staples to pass through the plurality of openings to tissue positioned between the inwardly facing surface of the anvil leg and the inwardly facing surface of the staple leg, and a cover device comprising at least one sheet comprising amnion attached to the inner surface of at least one of the anvil leg or the staple leg configured to attach to the tissue positioned between the inwardly facing surface of the anvil leg and the inwardly facing surface of the staple leg.

Clause 2: The cartridge of clause 1, wherein the at least one sheet comprises a one ply, two ply, three ply, or four ply amnion sheet.

Clause 3: The cartridge of clause 1 or clause 2, wherein the at least one sheet comprises a dried sheet comprising at least two layers of chorion-free amnion.

Clause 4: The cartridge of any of clauses 1-3, wherein the cover device is configured to transfer from the inwardly facing surface of the anvil leg or the staple leg to wetted tissue of a patient at a surgical site.

Clause 5: The cartridge any of clauses 1-4, wherein the at least one sheet has a thickness of from 20 μm to 100 μm.

Clause 6: The cartridge of any of clauses 1-5, wherein the at least one sheet is an elongated sheet having a width of about 5 mm to about 20 mm and a length of about 30 mm to about 90 mm, or preferably about 45 mm to about 60 mm.

Clause 7: The cartridge of any of clauses 1-6, wherein the cover device comprises at least one of a sleeve or a sock that is inserted over the anvil leg or the staple leg for securing the cover device to the anvil leg or the staple leg.

Clause 8: The cartridge of any of clauses 1-7, wherein the plurality of openings of the inwardly facing surface of the staple leg is arranged in a substantially linear pattern producing a stapled region that is from 1 to 3 staples in width and from 3 to 10 staples in length.

Clause 9: The cartridge of any of clauses 1-8, wherein the cartridge is configured to simultaneously release staples through each of the plurality of openings upon triggering of the surgical stapler creating at least one staple line through the tissue.

Clause 10: The cartridge of any of clauses 1-9, wherein the cartridge comprises a connector extending from a proximal end of the anvil leg or the staple leg, the connector being configured to engage a corresponding port of a handle of the surgical stapler for connecting the cartridge to the handle.

Clause 11: The cartridge of any of clauses 1-10, wherein the surgical stapler is a gastrointestinal stapler.

Clause 12: A cover device configured to be positioned on a leg of a surgical stapler and to transfer from the leg of the surgical stapler to tissue at a surgical site during a stapling procedure, the cover device comprising a removable backing; and at least one sheet comprising amnion attached to and in surface-to-surface contact with the removable backing, wherein the at least one sheet is configured to be attached to an inwardly facing surface of the leg of the surgical stapler and, once the backing is removed from the at least one sheet, to transfer from the leg to the tissue at the surgical site.

Clause 13: The cover device of clause 12, wherein the at least one sheet comprises a one ply, two ply, three ply, or four ply amnion sheet.

Clause 14: The cover device of clause 12 or clause 13, wherein the at least one sheet comprises a dried sheet comprising at least two layers of chorion-free amnion.

Clause 15: The cover device of any of clauses 12-14, wherein the at least one sheet is configured to transfer from the inwardly facing surface of the leg of the surgical stapler to a wetted surface.

Clause 16: The cover device of any of clauses 12-15, wherein the at least one sheet has a thickness of about 20 μm to about 100 μm.

Clause 17: The cover device of any of clauses 12-16, wherein the at least one sheet is an elongated sheet having a width of about 5 mm to about 20 mm and a length of about 30 mm to about 90 mm, preferably about 45 mm to about 60 mm.

Clause 18: The cover device of any of clauses 12-17, wherein the removable backing comprises at least one sheet of paper, cardboard, or opaque plastic.

Clause 19: The cover device of any of clauses 12-18, wherein the removable backing has a surface area that is larger than a surface area of the at least one sheet, such that the removable backing covers an entirety of an outwardly facing surface of the at least one sheet.

Clause 20: The cover device of clause 19, wherein the removable backing further comprises at least one portion for a user to grasp or hold that is not contacted by the at least one sheet.

Clause 21: An assembly method for a surgical stapler, the method comprising: applying at least one sheet comprising amnion to an inwardly facing surface of a leg of a stapler cartridge by pressing a surface of the at least one sheet against the inwardly facing surface of the leg of the surgical stapler; and removing a removable backing attached to the at least one sheet, thereby exposing an inwardly facing surface of the at least one sheet so that the at least one sheet can be attached to tissue of a patient during a stapling surgical procedure.

Clause 22: The method of clause 21, wherein the at least one sheet comprises a one ply, two ply, three ply, or four ply amnion sheet.

Clause 23: The method of clause 21 or clause 22, wherein the at least one sheet comprises a dried sheet comprising at least two layers of chorion-free amnion.

Clause 24: The method of any of clauses 21-23, wherein the cover device is configured to transfer from the inwardly facing surface of the leg of the surgical stapler to a wetted surface.

Clause 25: The method of any of clauses 21-24, wherein the at least one sheet has a thickness of about 20 μm to about 100 μm.

Clause 26: The method of any of clauses 21-25, wherein the at least one sheet is an elongated sheet having a width of about 5 mm to about 20 mm and a length of about 30 mm to about 90 mm, preferably about 45 mm to about 60 mm.

Clause 27: The method of any of clauses 21-26, wherein the surgical stapler comprises an anvil leg pivotally connected to a staple leg.

Clause 28: The method of clause 27, wherein applying the at least one sheet comprises applying a first amnion sheet to an inwardly facing surface of the anvil leg and a second amnion sheet to an inwardly facing surface of the staple leg.

Clause 29: The method of clause 27 or clause 28, further comprising, after removing the removable backing from the at least one sheet, pressing the tissue between the anvil leg and the staple leg of the surgical stapler and activating the surgical stapler causing a plurality of staples positioned in the staple leg to pass through the at least one sheet and the tissue creating a staple line.

Clause 30: A method for performing a surgical procedure, comprising: preparing a surgical stapler comprising a cartridge for the surgical procedure, wherein the cartridge comprises: an anvil leg comprising an inwardly facing surface; a staple leg pivotally connected to the anvil leg comprising a plurality of staples positioned in an interior of the staple leg and an inwardly facing surface configured to move towards the inwardly facing surface of the anvil leg, the inwardly facing surface comprising a plurality of openings positioned for the plurality of staples to pass through the plurality of openings, and a cover device comprising at least one sheet comprising amnion attached to the inner surface of at least one of the anvil leg or the staple leg; positioning patient tissue of a surgical site between the anvil leg and the staple leg of the cartridge; tightening the cartridge causing the staple leg to move toward the anvil leg and causing the at least one sheet to press against the patient tissue; and activating the surgical stapler causing the plurality of staples to pass from the staple leg through the patient tissue and the at least one sheet, thereby forming a staple line in the patient tissue.

Clause 31: The method of clause 30, wherein the at least one sheet comprises a one ply, two ply, three ply, or four ply amnion sheet.

Clause 32: The method of clause 30 or clause 31, wherein the at least one sheet comprises a dried sheet comprising at least two layers of chorion-free amnion.

Clause 33: The method of any of clauses 30-32, wherein the cover device is configured to transfer from the inwardly facing surface of the staple leg or the anvil leg of the surgical stapler to a wetted surface.

Clause 34: The method of any of clauses 30-33, wherein the at least one sheet has a thickness of about 20 μm to about 100 μm, a width of about 5 mm to about 20 mm, and a length of about 30 mm to about 90 mm, preferably about 45 mm to about 60 mm.

Clause 35: The method of any of clauses 30-34, wherein the cover device comprises at least one of a sleeve or a sock that is inserted over the anvil leg or the staple leg for securing the cover device to the anvil leg or the staple leg.

Clause 36: The method of any of clauses 30-35, wherein the surgical procedure comprises an intestinal anastomosis procedure.

Clause 37: The method of any of clauses 30-36, wherein the surgical procedure forms a side-by-side anastomosis between a first tubular section of a gastrointestinal (GI) tract of the patient and a second tubular section of the GI tract of the patient, and wherein positioning the patient tissue between the anvil leg and the staple leg comprises inserting the anvil leg through an incision into a lumen of the first tubular section and inserting the staple leg through an incision into a lumen of the second tubular section.

Clause 38: The method of clause 37, wherein the first tubular section and/or the second tubular section comprise a portion of an intestine or bowel of the patient.

Clause 39: The method of clause 37 or clause 38, wherein activating the surgical stapler causes the plurality of staples to pass through the at least one sheet and through portions of the first tubular section and the second tubular section, thereby connecting the first tubular section to the second tubular section.

Clause 40: The method of clause 39, further comprising forming an incision through the at least one sheet and side surfaces of the first tubular section and the second tubular section, thereby forming a passage between a lumen defined by the first tubular section and a lumen of the second tubular section.

Clause 41: The method of clause 39 or clause 40, wherein connecting the first tubular section to the second tubular section places the first lumen in fluid communication with the second lumen.

Clause 42: The method of any of clauses 39-41, further comprising forming a staple line over open ends of the first tubular section and the second tubular section through another at least one sheet comprising amnion, thereby sealing the open ends of the first tubular section and second tubular section and forming an enclosed lumen defined by the first tubular section and the second tubular section.

Clause 43: The method of any of clauses 30-42, wherein preparing the surgical stapler comprises attaching a pre-assembled cartridge comprising the at least one sheet comprising amnion attached to the anvil leg or the staple leg of the cartridge to the surgical stapler by engaging a connector of the cartridge to a corresponding port of the surgical stapler.

Clause 44: The method of any of clauses 30-43, wherein preparing the surgical stapler comprises obtaining a cover device comprising a removable backing and the at least one sheet comprising amnion, pressing a surface of the at least one sheet against the inwardly facing surface of the anvil leg or the staple leg, and removing the removable backing from the at least one sheet, such that the at least one sheet remains attached to the inwardly facing surface of the anvil leg or the staple leg.

Clause 45: The method of any of clauses 30-44, wherein the surgical procedure is a robot-assisted surgical procedure, and wherein positioning the patient tissue, tightening the cartridge, and/or activing the surgical stapler are automatically performed using a surgical robot system comprising at least one arm that moves and actuates a surgical stapler.

Clause 46: An implantable surgical cover device configured to be implanted over tissue of a patient at a surgical site during a surgical stapling procedure, the cover device comprising: at least one sheet comprising at least one layer of amnion, wherein the at least one sheet comprises a first surface, a second surface, and a peripheral edge extending between the first surface and the second surface; at least one opening extending through the at least one sheet provided to guide a user for proper positioning of the surgical stapler during the surgical procedure; and one or more markings printed or embossed on the at least one sheet showing proper positioning for a staple line provided by the surgical stapler.

Clause 47: The cover device of clause 46, wherein the at least one layer of amnion comprises a dried sheet of chorion-free amnion.

Clause 48: The cover device of clause 46 or clause 47, wherein the at least one sheet comprises a one ply, two ply, three ply, or four ply amnion sheet.

Clause 49: The cover device of any of clauses 46-48, wherein the at least one sheet is a dried sheet comprising at least two layers of chorion-free amnion.

Clause 50: The cover device of any of clauses 46-49, wherein the at least one sheet is a square shape with an edge of from about 4 cm to about 8 cm in length, and wherein the at least one annular opening has a diameter of from about 5 mm to about 20 mm.

Clause 51: The cover device of any of clauses 46-50, wherein the at least one opening is sized to permit an anvil portion of a circular surgical stapler to pass through the at least one opening.

Clause 52: The cover device of any of clauses 46-51, wherein the at least one sheet is rectangular and the at least one annular opening is offset from a center of the at least one sheet by at least 0.5 cm in at least one direction.

Clause 53: The method of any of clauses 46-52, wherein the at least one opening comprises a diameter that is slightly larger than a diameter of the anvil portion, thereby allowing the anvil to pass through the annular opening without contacting the at least one sheet.

Clause 54: The method of clause 53, wherein the diameter of the at least one opening is about 1%, 2%, 3%, 4%, 5%, 6%, 7%, 8%, 9%, or 10% larger than the diameter of the anvil portion of the circular surgical stapler.

Clause 55: The method of clause 53 or clause 54, wherein the at least one opening is offset from a center of the surface of the sheet.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1A is a schematic drawing of an implantable cover device for positioning on or proximate to a surgical site, according to an aspect of the present disclosure;

FIG. 1B is a schematic drawing of another example of an implantable cover device for positioning on or proximate to a surgical site, according to an aspect of the present disclosure;

FIG. 1C is a cross-sectional view of the cover device of FIG. 1A taken along line 1C-1C (in FIG. 1A), according to an aspect of the present disclosure;

DETAILED DESCRIPTION OF THE INVENTION

Figures 2A, 2B:
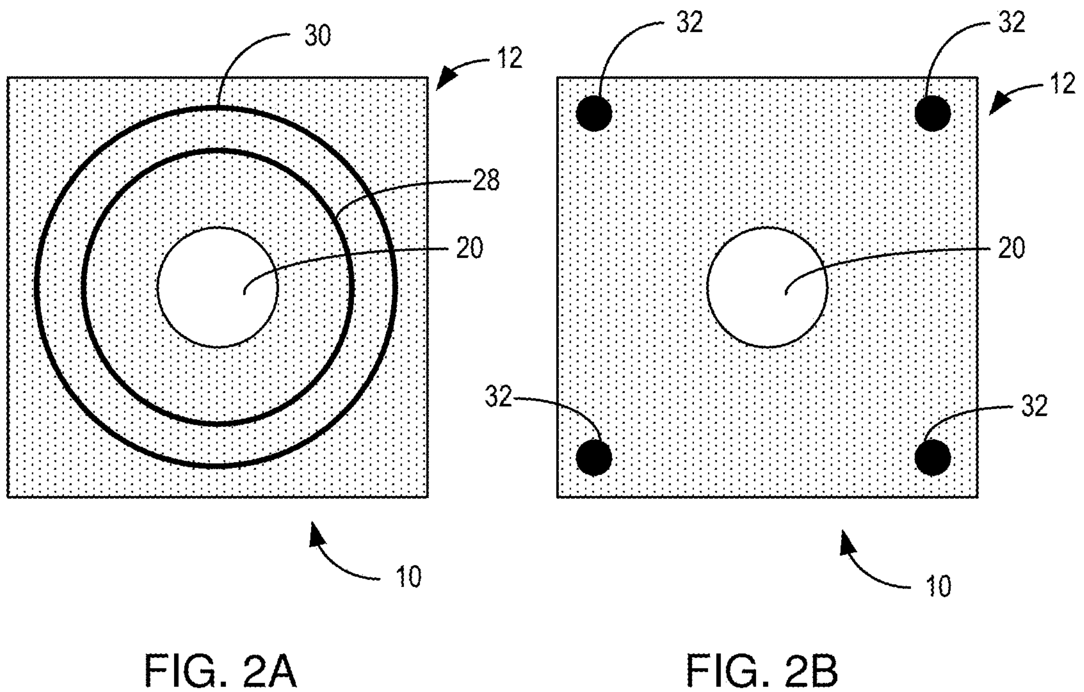
FIG. 2A is a schematic drawing of another example of an implantable cover device for positioning on or proximate to a surgical site, according to an aspect of the present disclosure.
FIG. 2B is a schematic drawing of another example of an implantable cover device for positioning on or proximate to a surgical site, according to an aspect of the present disclosure.

As used herein, the singular form of "a", "an", and "the" include plural referents unless the context clearly states otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the "patient" can be any species of the human or animal kingdom having a gastrointestinal tract including, for example, intestines, colon, and/or rectum. Non-limiting examples of patients include mammal(s), such as human(s) and/or non-mammalian animal(s). Non-limiting examples of mammal(s) include primate(s) and/or non-primate(s). Primate(s) include human(s) and non-human primate(s), including but not limited to male(s), female(s), adult(s) and children. Non-limiting examples of non-human primate(s) include monkey(s) and/or ape(s), for example chimpanzee(s). Non-limiting examples of non-primate(s) include cattle (such as cow(s), bull(s) and/or calves), pig(s), camel(s), llama(s), alpaca(s), horse(s), donkey(s), goat(s), rabbit(s), sheep, hamster(s), guinea pig(s), cat(s), dog(s), rat(s), mice, lion(s), whale(s), and/or dolphin(s). Non-limiting examples of non-mammalian animal(s) include bird(s) (e.g., duck(s) or geese), reptile(s) (e.g., lizard(s), snake(s), or alligator(s)), amphibian(s) (e.g., frog(s)), and/or fish. In some examples, the animals can be zoological animals, human pets and/or wild animals.

For the purposes of this specification, unless otherwise indicated, all numbers expressing quantities of ingredients, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention. As used herein, the term "about" means "close to" and that variation from the exact value that follows the term is within amounts that a person of skill in the art would understand to be reasonable. For example, when the term "about" is used with respect to a numerical value, the value may vary within a reasonable range, such as within +/−10%, +/−5%, or +/−1% of the stated value. Notwithstanding that the numerical ranges and parameters setting forth the broad scope of the invention are approximations, the numerical values set forth in the specific examples are reported as precisely as possible. Any measured numerical value, however, may inherently contain certain errors resulting from the standard deviation found in their respective testing measurements. Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

With reference to the figures, the present disclosure is directed to medical devices, such as a substrate, patch, bandage, or cover device 10, configured to be implanted at a surgical site and to surgical methods for positioning and fixation of such devices 10. In some examples, the cover devices 10 disclosed herein can be configured to be connected to or integrated with existing surgical tools, such as a surgical stapler. For example, the cover device 10 can be a sleeve or sock that attaches to and/or is positioned over or on a tissue contacting part of the surgical tool. The cover device can be configured to easily move or deploy from the surgical tool to the surgical site without requiring additional or extra actions by the surgeon or care provider. Instead, the surgeon or care provider can simply use the surgical tool in the conventional manner. During normal use of the surgical tool, the cover device can be configured to automatically transfer from the surgical tool to the surgical site without requiring additional actions by the surgeon.

In some examples, the medical devices and surgical methods disclosed herein are intended for use in surgical procedures, particularly anastomosis surgical procedures, namely formation of an end-to-end, end-to-side, and/or side-to-side anastomosis between tubular structures (e.g., a bowel or intestine) of a patient's GI tract.

The medical devices and methods of the present disclosure use sheet(s) of protective material, such as sheets or layers comprising amnion layer(s) and/or an amnion scaffold, for improving safety of anastomosis surgical procedures, reducing leakage, bleeding, inflammation, and rupture. In some examples, the protective material of the medical device (e.g., the substrate or cover device 10) is a single layer or multi-layer (e.g., two ply, three ply, or four ply) sheet comprising amnion. In some examples, the amnion sheet is the EvoPatch® implantable patch manufactured by Evologics, LLC of San Antonio, TX, which is a double-layer, chorion-free, dried patch.

In some examples, the protective material or sheet comprises amnion that is free from chorion. A sheet that is entirely amnion and/or is chorion-free is believed to have superior wound healing properties compared to sheets or materials that include less (e.g., a lower concentration) of amnion. Furthermore, by removal of chorion materials, maternal antigen and Class II antigens are removed, reducing the risk of rejection and immune-responsiveness. Also, it has been found that a sheet comprising two layers of amnion can be 70% stronger and less than half the thickness of comparable amnion/chorion patches.

As is known in the art, amnion graft material can be used to help treat wounds by, for example, providing nutrients for damaged tissue, sealing damaged blood vessels, and/or reducing bleeding. In particular, the amnion material can include nutrients for encourage tissue growth and healing, which makes amnion suitable for wound treatment, as well as for reducing infection. Amnion is also known to provide anti-inflammatory benefits, epithelialization and/or healing benefits, and scar tissue suppression benefits. The amnion material, such as decellularized and/or devitalized amnion, of the cover device 10 can be provided in a dried state (e.g., dehydrated and terminally-sterilized) and, as such, can adhere to tissue, such as surgically-repaired tissue. In particular, a dried sheet of amnion adheres to wetted patient tissues without adhesives, meaning that the cover devices 10 disclosed herein can be easily adhered to surgical sites during surgical procedures without needing to prepare the surgical site or cover device 10 for adhesion.

The present inventor has recognized that adherence of a protective material or barrier to a surgical site can reduce leakage and bleeding. However, conventional practices for introducing such barrier structures over a wound are often imprecise or incomplete. Furthermore, such implanted sheets often detach from biological tissue (e.g., at an intestinal surface) during or after surgery (referred to as either immediate or delayed migration) and/or anastomotic coverage is often incomplete. In order to address such deficiencies, the medical devices disclosed herein are configured to be fixed to the surgical site by, for example, staples, sutures, and/or glue, providing a complete and stable seal over an anastomosis.

In some examples, the amnion sheet is not intended to act solely as a barrier or buttress that augments structural stability of a staple line. Instead, the amnion sheet or graft is provided to supplement, enhance, and accelerate the healing process locally. Thus, the healing benefits of amnion, along with its anti-adhesive and anti-inflammatory benefit, are provided directly to the gastrointestinal staple line by the anastomosis methods and devices disclosed herein.

In some examples, the surgical methods of the present disclosure can be implemented in open, laparoscopic, and robotic surgeries. For example, actions such as positioning or deployment of the medical device (e.g., the substrate or cover device 10) and/or fixation of the medical device to the surgical site by stapling and/or sutures can be performed using a robotic-assisted surgical system comprising a robotic arm that supports and manipulates a tool, such as a surgical stapler. An exemplary robotic-assisted surgical system that can be used with the medical devices and surgical methods disclosed herein is the Da Vinci™ Robotic-Assisted Surgery system manufactured by Intuitive Surgical, Inc. of Sunnyvale, CA.

Implantable Cover Device for Anastomosis Procedure

FIGS. 1A-IC show examples of medical devices, referred to herein as an implantable surgical cover devices 10, configured to be implanted over tissue of a patient at a surgical site during a surgical procedure, such as an anastomosis surgical procedure. The cover devices 10 comprises a substrate, such as a bandage or sheet 12, which includes layers of amnion (also referred to as amnion graft material). As previously described, the amnion sheet can be similar to and/or can include the same materials as the EvoPatch® by Evologics, LLC.

In some examples, as shown in FIG. 1C, the sheet 12 can include two layers 26*a*, 26*b* of amnion, such as dried amnion, that are laminated or adhered together to provide additional integrity, strength, and content of beneficial agents. Each amnion layer 26*a*, 26*b* can have a thickness of about 25 μm to about 50 μm, preferably about 44 μm, providing a total, dual-layer thickness of about 50 μm to about 100 μm, preferably about 88 μm. The amnion layers 26*a*, 26*b* can be identical in chemical composition and configured to remain adhered together as the layers degrade. In some examples, the layers can detach or delaminate from each other as the sheet 12 degrades. In other examples of the cover device 10, the layers 26*a*, 26*b* can be different types of amnion or different materials depending upon therapeutic requirements for a particular procedure being performed. For example, an inner-most layer 26*a* (e.g., a layer configured to contact patient tissue) can comprise chorion-free, dried amnion. The outer-most layer 26*b* can comprise another type of amnion or another material.

The sheet 12 can include a first or outwardly facing surface 14 configured to face away from the patient tissue, a second or inwardly facing surface 16 configured to contact and/or adhere to patient tissue, and a peripheral edge 18 extending between the outwardly facing surface 14 and the inwardly facing surface 16. In some examples, the outwardly facing surface 14 and the inwardly facing surface 16 of the sheet 12 are identical and are both capable of being attached and/or adhered to patient tissue. In other examples, only the inwardly facing surface 16 comprises dried amnion and is configured to contact the patient tissue, while the outwardly facing surface 14 can be formed from a different material that does not adhere to patient tissue.

Figure 3A:
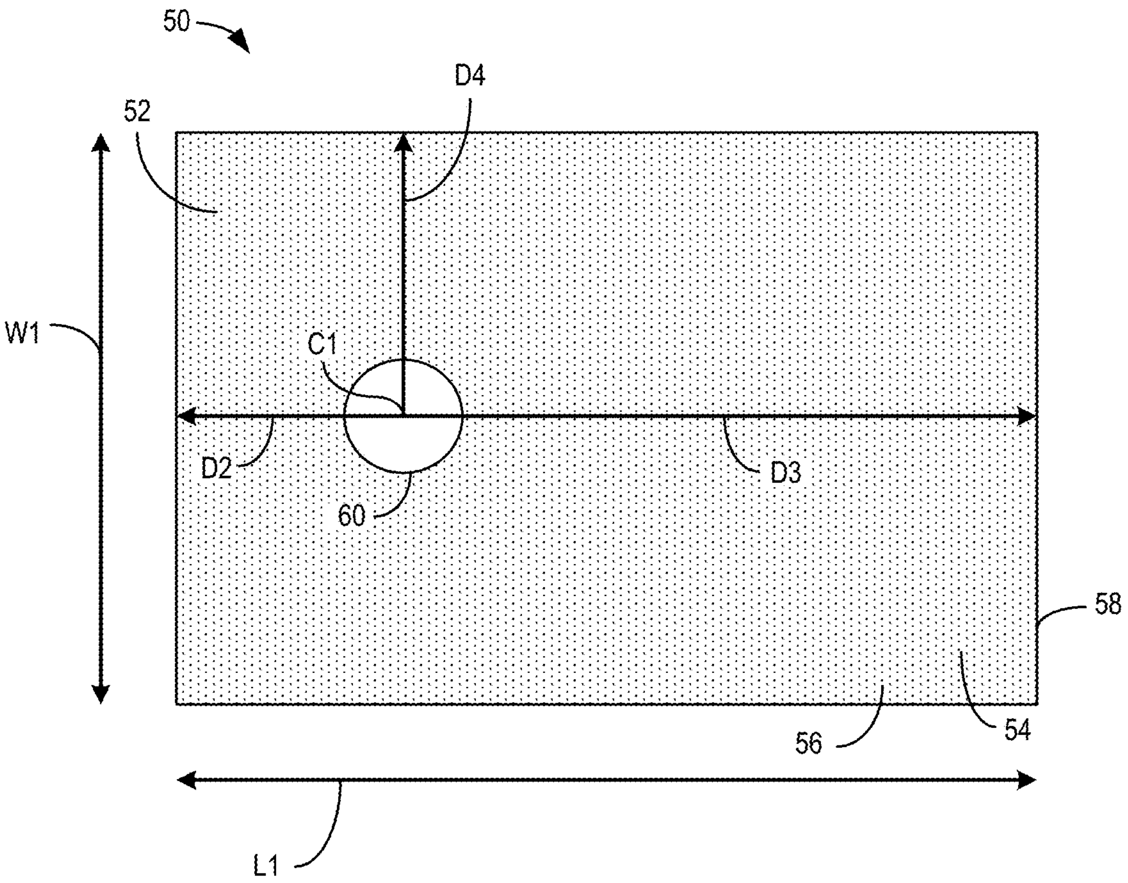
FIG. 3A is a schematic drawings of another example of an implantable cover device for positioning on or proximate to a surgical site, according to an aspect of the present disclosure.

The sheet 12 can be any convenient shape and size sufficient for positioning over surfaces, tissues, openings, apertures, or incisions at a surgical site. For example, as shown in FIGS. 1A and 1B, the sheet 12 can be a square with a side of length S1. The length S1 can be, for example, from about 4 cm to about 8 cm, or preferably about 6 cm. A square device 10 with a 6 cm side S1 can accommodate a staple line of up to about 8.49 cm by aligning along diameter of the tissue diagonally as shown in FIG. 1B. In other examples, as shown in FIG. 3A, the sheet 52 can be a rectangle, such as a 4 cm by 8 cm rectangular sheet or a 5 cm by 7 cm rectangular sheet.

The cover device 10 also includes an opening 20 extending through the sheet 12. The opening 20 can be an annular or enclosed opening 20 that is fully surrounded by the sheet 12. As shown in FIGS. 1A and 1B, the opening 20 is depicted as a circle. In other examples, the opening 20 can be any other regular or irregular shape, such as an oval, square, rectangle, or any other convenient and/or useful shape, for example depending on the shape and size of a surgical tool being used for the procedure being performed.

The opening 20 can be positioned on the sheet 12 to guide the surgeon in proper positioning of a surgical tool, such as an anvil of a surgical stapler. For example, as described in further detail in the following description of anastomosis methods, the surgeon may position the cover device 10 on patient tissue and then insert parts of a surgical tool, such as the anvil portion of the surgical stapler, through the opening 20 of the cover device 10. As shown in FIGS. 1A and 1B, the opening 20 can be positioned in the center of the sheet 12. The opening 20 can be sized and/or configured to permit passage of the anvil of the surgical stapler through the annular opening 20. The opening 20 can have a diameter D1 that is slightly larger than an outer diameter of the anvil portion of the surgical stapler. For example, the diameter of the annular opening 20 can be about 1%, 2%, 3%, 4%, 5%, 6%, 7%, 8%, 9%, or 10% larger than the diameter of the anvil portion of the circular surgical stapler. In some examples, the diameter D1 of the opening 20 is about 5 mm to about 20 mm.

The cover devices 10 disclosed herein can be very thin and become transparent when wetted with fluids. To improve visualization for a wetted cover device 10, the cover device 10 can include one or more markings on the sheet 12. For example, guidelines or markings can be provided on the cover device 10 for assisting the surgeon in positioning a surgical stapler and/or activating the stapler to form a staple line. The marking can be colorized and/or radiopaque to improve visualization.

As shown in FIG. 1A, in some examples, the marking can be a circular staple guide 22 that assists the surgeon in forming a staple line between sides of a square shaped sheet 12. In other examples, as shown in FIG. 1B, the staple line can be an oval-shape staple guide 22 extending between, for example, a lower left corner of the sheet 12 and an upper right corner of the sheet 12. The markings or staple guide 22 can be printed markings formed from a biocompatible and/or non-toxic dye or ink. In other examples, the markings can be embossed, etched, or pressed into the sheet 12. In other examples, the markings can be elongated members, such as radiopaque bands, strips, or wires, which are adhered to or embedded in the sheet 12. For example, radiopaque bands can be laminated between layers 26*a*, 26*b* of a dual-layer amnion sheet 12.

FIGS. 2A and 2B show examples of cover devices 10 with different types of markings positioned to assist in visualization of the cover device 10 during surgical placement. As depicted in FIGS. 2A and 2B, the cover devices 10 include the amnion sheet 12 and the opening 20. In FIG. 2A, the cover device 10 also includes multiple circumferential markers or rings, such as an inner ring 28 and an outer ring 30. The multiple markers or rings 28, 30 can function as a bulls-eye or target helping the surgeon to visualize where the surgical tool, such as a portion of the stapler, should be positioned. In FIG. 2B, the cover device 10 includes dots 32 positioned proximate to corners of the square shaped sheet 12. As in previous examples, the markings or dots 32 can be separate materials or members adhered to or embedded within the amnion sheet 12. The rings 28, 30 or dots 32 can also be printed (e.g., using a biocompatible and/or non-toxic dye or ink), embossed, or pressed into the sheet 12.

FIG. 3A is a schematic drawing showing another example of an implantable surgical cover device 50, configured to be implanted over tissue of a patient at a surgical site during a surgical procedure, such as an anastomosis surgical procedure. As in previous examples, the cover device 50 comprises a substrate, such as a bandage or sheet 52, which includes at least one layer of amnion (also referred to as amnion graft material). As previously described, the amnion sheet can comprise two amnion layers, such as a double-layer, chorion-free, dried substrate or sheet 52. The sheet 52 can include the same materials as the EvoPatch® by Evologics, LLC. The cover device 50 can also include any of the previously described guides or markings printed, embossed, or embedded on the sheet 52. For example, the cover device 50 can include staple lines showing the surgeon proper positioning for the surgical tool, as well as rings or dots to help with visualization of the sheet 52 when it is wetted and/or adhered to patient tissue.

As in previous examples, the sheet 52 can also include a first or outwardly facing surface 54 configured to face away from the patient tissue, a second or inwardly facing surface 56 configured to contact and/or adhere to patient tissue, and a peripheral edge 58 extending between the outwardly facing surface 54 and the inwardly facing surface 56. As in previous examples, the outwardly facing surface 54 and the inwardly facing surface 56 of the sheet 52 can be identical, meaning that both surfaces 54, 56 are capable of being attached and/or adhered to patient tissue.

As shown in FIG. 3A, the sheet 52 is a rectangle. For example, the sheet can be a 5 cm by 7 cm rectangle. In other examples, the sheet 52 can be a 4 cm by 8 cm rectangle. The cover device 50 also includes an opening 60 extending through the sheet 52. The opening 60 can be annular or enclosed meaning that the opening 60 is fully surrounded by the sheet 52. Unlike in previous examples, which included a centered opening, the opening 60 in FIG. 3A is offset from the center of the sheet 52. For example, the opening 60 can be offset by a distance of about 0.5 cm to 1.5 cm from a center of the sheet in any direction (e.g., either a horizontal or a vertical direction). As shown in FIG. 3A, in one non-limiting example, a center CI of the annular opening 60 can be a distance D2 of 2.0 cm from one side of the sheet 52 and a distance D3 of 5.0 cm from an opposing side of the sheet 52. As shown in FIG. 3A, the opening 60 is spaced an equal distance (e.g., a distance D4 of 2.5 cm) from a top edge and a bottom edge of the sheet 52. However, in other examples, the offset opening 60 can be positioned at other locations on the sheet 52 depending on therapeutic requirements of a procedure being performed. For example, the opening 60 may be positioned closer to a top edge or a bottom edge of the sheet 52 in some examples.

As described in further detail in connection the surgical methods of the present disclosure, the offset opening 60 is provided to guide the surgeon in positioning an anvil portion of a surgical stapler in a location that is offset from a central axis of lumen(s) of sections or segments being connected together. In some instances, positioning the surgical stapler at this offset (e.g., spaced apart from the central axis of the tubular section) location allows the surgeon to create an angled end-to-end anastomosis. Also, in some cases, leakage or bleeding of an end-to-end anastomosis is more likely to occur near sides or edges of tissue being stapled together. Therefore, surgeons may wish to position the stapler nearer to such areas to prevent leaks from occurring in such potentially problematic locations. The cover device 50 with the offset annular opening 60 can guide the surgeon in positioning of the surgical stapler proximate to these problematic locations.

As in previous examples, the opening 60 can be sized and/or configured to permit passage of the anvil of the surgical stapler through the opening 60. For example, the opening 60 can have a diameter that is slightly larger than an outer diameter of the anvil portion of the surgical stapler. In some examples, the diameter of the opening 60 can be about 5 mm to about 20 mm.

Figure 3B:
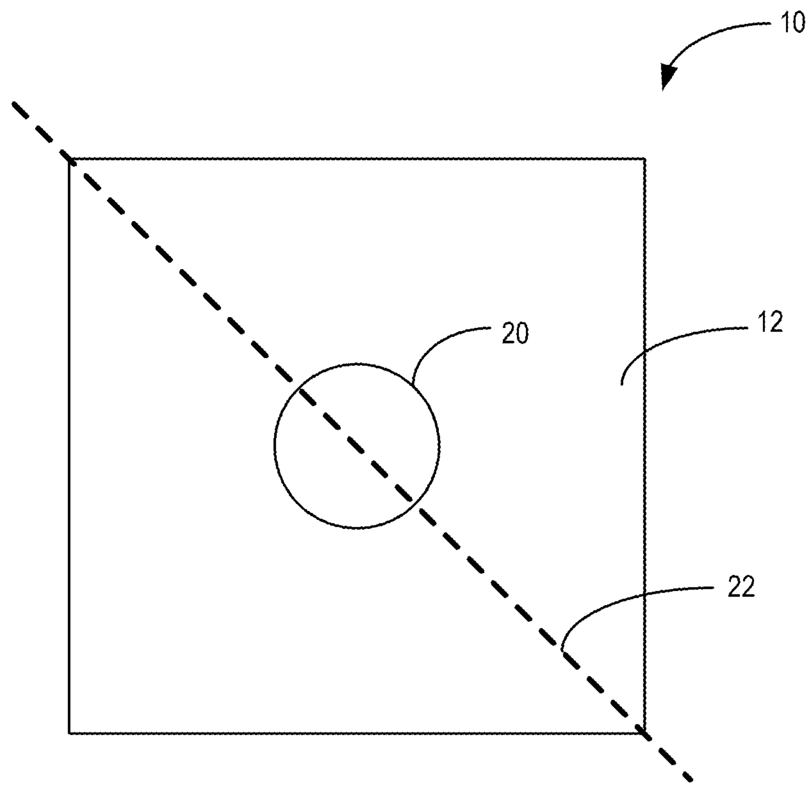
FIG. 3B is a schematic drawings of another example of an implantable cover device for positioning on or proximate to a surgical site, according to an aspect of the present disclosure.

FIG. 3B shows another example of a cover device 10, which can be used in a procedure for forming an end-to-end anastomosis. The cover device 10 is configured to be placed on a diagonal over the surgical site. The cover device 10 includes a marking or guide line 22 showing that a diagonal staple line should be formed. Specifically, the guide line 22 extends between a top left corner and a bottom right corner of the cover device 10, which extends over the opening 20 of the cover device 10. The diagonal staple line allows for longer staple line coverage compared to staple lines extending between opposing sides of the cover device 10. For example, for a 6 cm square sheet, a staple line between sides of the cover device 10 is 6 cm in length, while a staple line extending between opposing corners of the cover device 10 or sheet 12 is 8.48 cm in length.

Cover Device for Attachment to a Surgical Stapler

In some examples, a cover device 210 can be adapted to be attached to a surgical tool, such as a stapler, immediately prior to performing the surgical procedure and to remain secured to the surgical tool while advancing the tool to a surgical site. For example, an amnion sheet of the cover device 210 can be configured to remain attached to a surgical tool while the tool is advanced through a port, tube, or catheter to a surgical site during a laparoscopic or robotic procedure. Positioning the amnion sheet on the surgical tool, such as a leg of a surgical stapler, may reduce or eliminate a learning curve for operative placement of the amnion sheet for open, laparoscopic, and/or robotic surgical procedures. In particular, once the amnion sheet is positioned on the surgical tool, the surgeon may simply position the tool and press the tool against patient tissue as occurs in conventional or current surgical procedures. The amnion sheet can then automatically transfer or be deployed to the patient tissue while tightening components of the tool together and/or upon activation of the tool. In some examples, once deployed at a surgical site, the amnion sheet can be imparted to the serosa of the gastrointestinal tissue along with, for example, staples deployed from a surgical stapler.

In some examples, the surgical tool can be a surgical stapler that produces a staple line or elongated staple region, which includes a staple leg and an anvil leg for deploying lines of staples. Such staplers are known in the art and commercially available from multiple manufactures including Ethicon US, LLC and Medtronic plc. The surgical stapler can also be a tool configured to be manipulated by a robotic-assisted surgery system. An exemplary surgical stapler, which can be used with the cover devices and surgical methods of the present disclosure, is disclosed in U.S. Pat. No. 8,453,908 entitled "Surgical stapling instrument with improved firing trigger arrangement," which is incorporated herein by reference in its entirety.

Figures 4A, 4B:
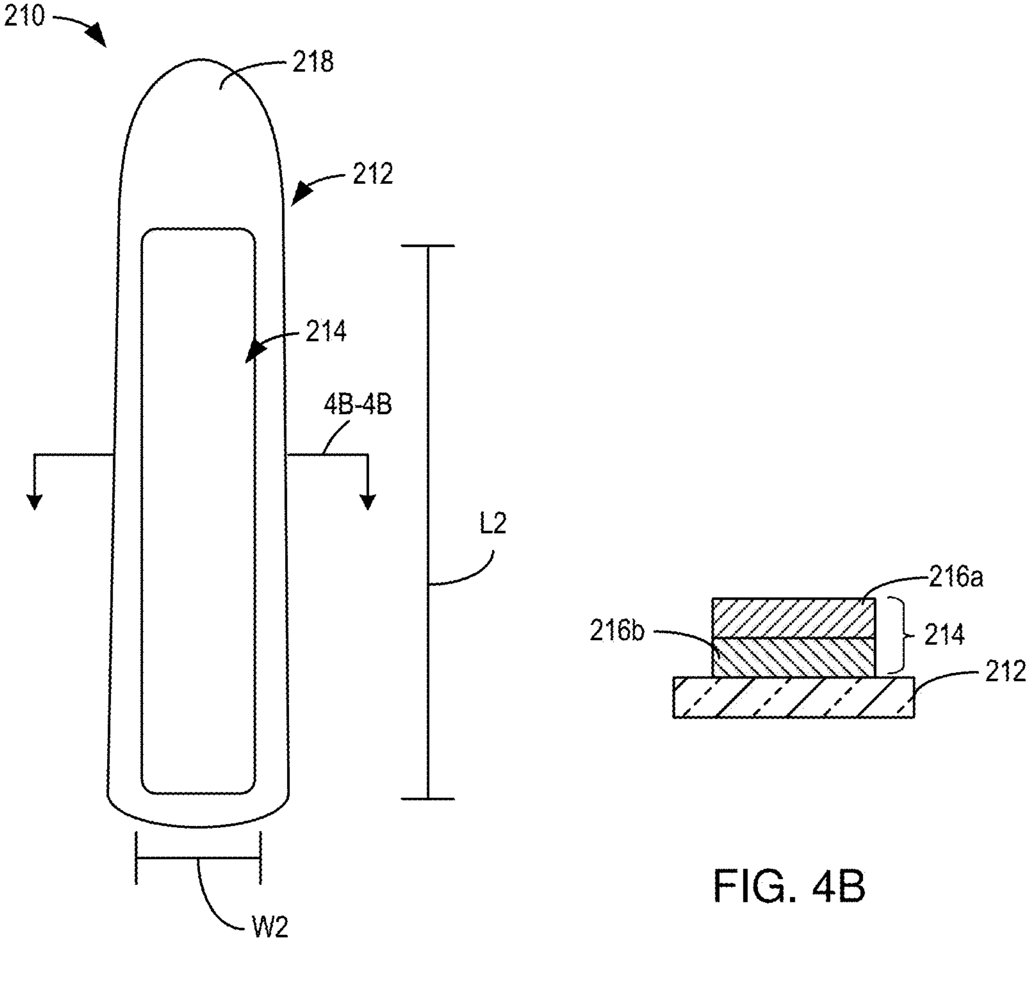
FIG. 4A is a schematic drawing of a cover device including a removable backing, according to an aspect of the present disclosure.
FIG. 4B is a schematic drawing of a cross-sectional view of the cover device of FIG. 4A taken along line 4B-4B (in FIG. 4A), according to an aspect of the present disclosure.

FIGS. 4A and 4B are schematic drawings showing an exemplary cover device 210, similar to a sticker or adhesive decal, configured to be positioned on a leg of a surgical stapler. The cover device 210 is configured to transfer from the leg of the surgical stapler to tissue at a surgical site during a stapling procedure. In particular the cover device 210 is configured to adhere and/or remain connected to a wetted surface, such as wetted patient tissue at the surgical site. The cover device 210 includes a removable backing 212, such as paper (e.g., waxed paper), cardboard, opaque plastic, or similar materials, and a sheet 214 comprising layers 216*a*, 216*b* (shown in FIG. 4B) of amnion attached to and in surface-to-surface contact with the removable backing 212. The amnion sheet 214 is configured to be attached to an inwardly facing surface of a leg of the surgical stapler and, once the backing 212 is removed from the amnion sheet, 214 to transfer from the leg to the tissue at the surgical site. Desirably, the backing 212 comprises a slippery or smooth surface so that the amnion sheet 214 can be easily removed from the backing 212 without tearing, folding, or otherwise damaging the amnion sheet 214.

As in previous examples, the amnion sheet 214 can include one or more amnion layers 216*a*, 216*b*. For example, the sheet 214 can be a one ply, two ply, three ply, or four ply amnion sheet. In some examples, the sheet 214 comprises a dried sheet comprising at least two layers 216*a*, 216*b* of chorion-free amnion. Each layer 216*a*, 216*b* of amnion can have a thickness of from about 20 μm to about 50 μm, preferably about 44 μm. Therefore, a two-play amnion sheet can have a total, dual-layer thickness of about 40 μm to about 100 μm, or preferably about 88 μm.

The sheet 214 of the cover device 210 is sized to be connected to the staple portion or the anvil portion of a surgical stapler. In some examples, the cover device 210 can include an elongated sheet 214 sized to be connected to and substantially cover the leg of the surgical stapler. In that case, the sheet 214 can have a width W2 (shown in FIG. 4A) of about 5 mm to about 20 mm and a length L2 (shown in FIG. 4A) of about 30 mm to about 90 mm, preferably about 45 mm to about 60 mm. In other examples, the sheet 214 can be sized to be attached to the anvil portion of a circular surgical stapler. In such instances, the sheet 214 can be circular having a diameter that is the same as or slightly larger than a diameter of the anvil portion of the circular stapler.

The removable backing 212 can be sized so that that the cover device 210 is easy to pick-up and manipulate with one hand. Also, the removable backing 212 should be easy to remove so as not to be a distraction during performance of a surgical procedure. In order to provide suitable maneuverability, the removable backing 212 can be larger than the amnion sheet 214. In particular, the removable backing 212 can have a surface area that is larger than a surface area of the sheet 214, such that the removable backing 212 covers an entirety of an outwardly facing surface of the sheet 214. In some example, the removable backing 212 can include a portion for grasping or holding, which is not contacted by the sheet 214. For example, as shown in FIGS. 4A and 4B, the removable backing 212 includes a tab 218 sized to be held, for example, between an index finger and thumb of the surgeon or another individual who prepares the surgical tool, such as the stapler, for use.

Assembly Method for a Surgical Stapler

Figure 6:
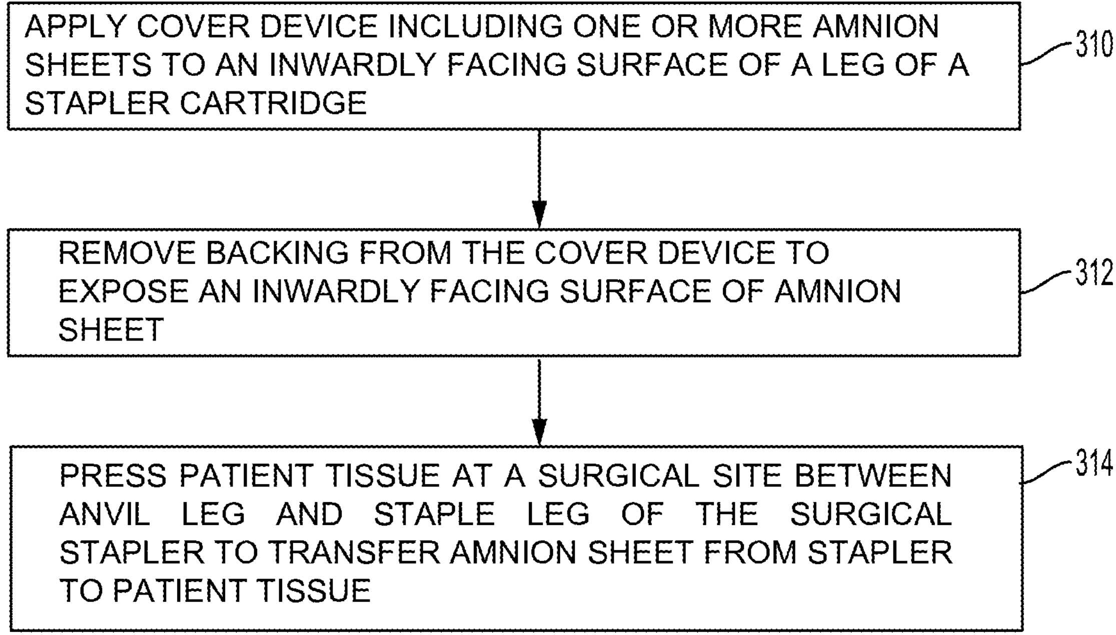
FIG. 6 is a flow chart showing steps for assembling a surgical stapler for use in performing a surgical procedure, according to an aspect of the present disclosure.

FIG. 6 is a flow chart showing steps for assembling a surgical stapler for use in performing a surgical procedure. At step 310, the method comprises applying a cover device 210, which includes one or more amnion sheets 214, to an inwardly facing surface of a leg of a stapler cartridge. For example, a surgeon or another individual tasked with preparing the surgical stapler for use may press the cover device 210 against the cartridge such that a surface of the amnion sheet(s) 214 contacts and adheres to an inwardly facing surface of the leg of the cartridge. As in previous examples, the amnion sheet(s) 214 of the cover device 210 can include one or multiple amnion layers 216*a*, 216*b* (e.g., can include a one ply, two ply, three ply, or four ply amnion sheet 214) having a total thickness of from about 20 μm to 100 μm depending upon the number of sheets or layers 216*a*, 216*b* present in the cover device 210.

The amnion sheet(s) 214 of the cover device 210 can have a size and shape corresponding to the size and shape of the staple leg or anvil leg of the surgical stapler. For example, the amnion sheet(s) 214 can be generally elongated or rectangular in shape having a width of about 5 mm to 20 mm and a length of 30 mm to 90 mm or, preferably, from 45 mm to 60 mm.

In some examples, the amnion sheet 214 comprises a dried sheet comprising at least two layers of chorion-free amnion. As previously described, a dried amnion sheet adheres easily to wetted surfaces even without using an adhesive. As such, connecting the amnion sheet 214 to the leg of the cartridge can include wetting a surface of the cartridge leg and then contacting the amnion sheet 214 to the wetted surface.

Figure 5A:
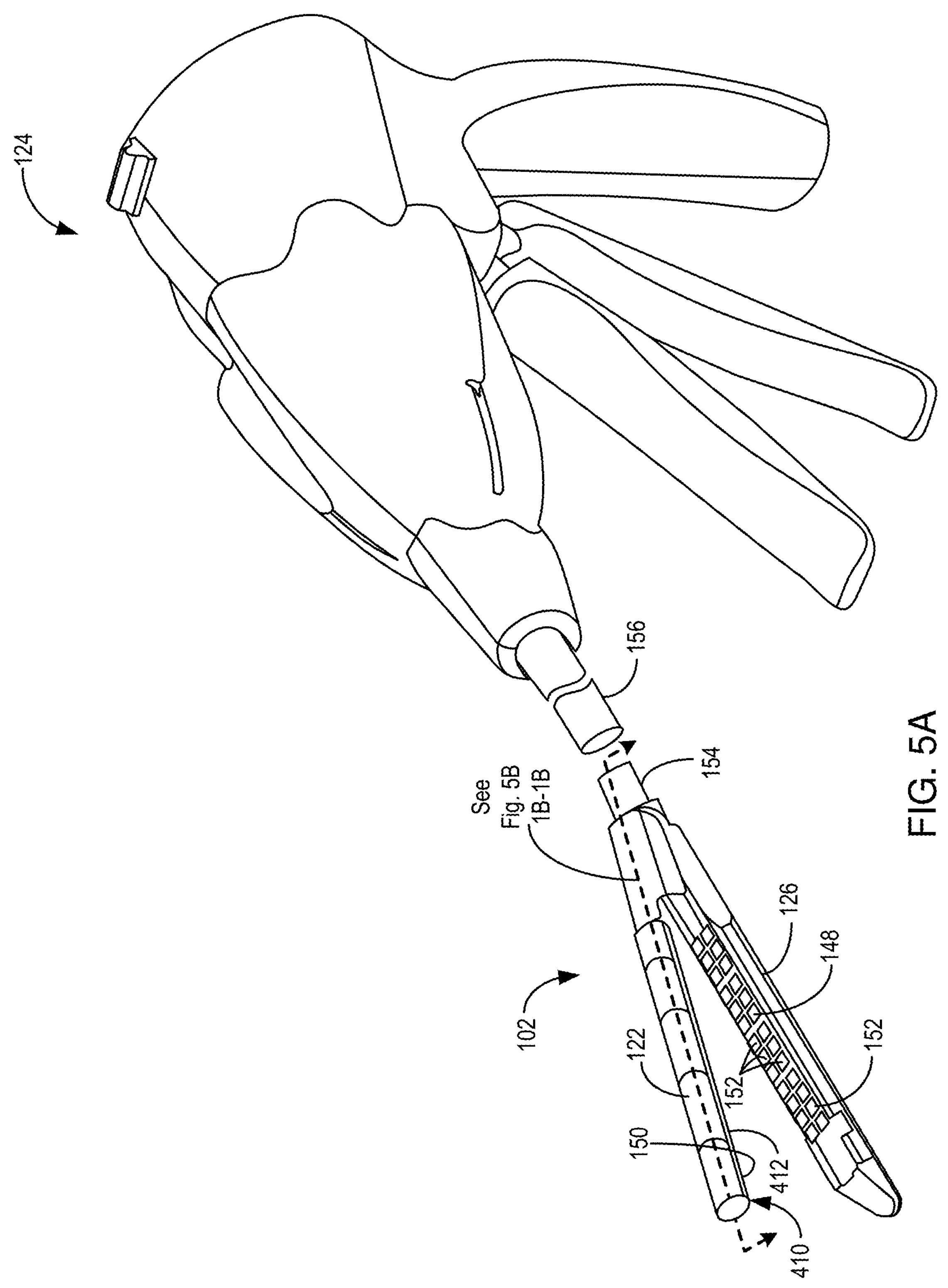
FIG. 5A is a perspective view of a surgical stapler and cartridge, according to an aspect of the present disclosure.
Figure 5B:
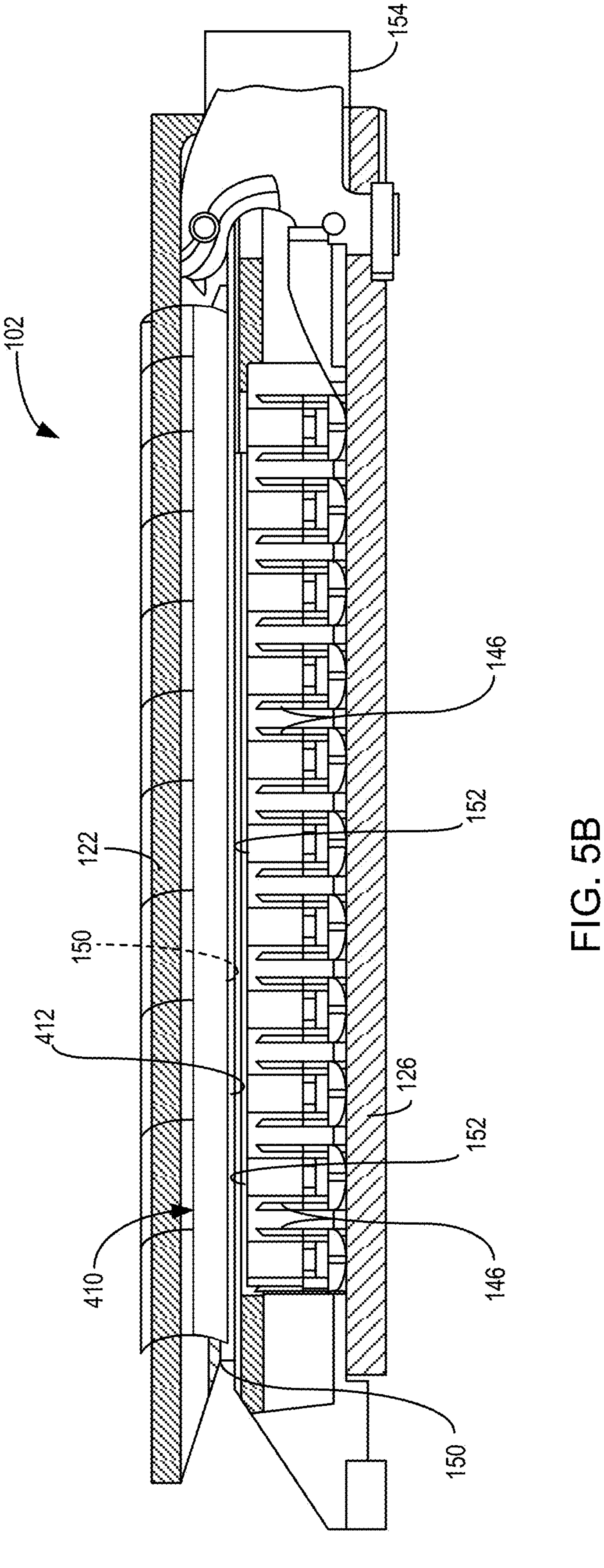
FIG. 5B is a cross-sectional view of the cartridge of FIG. 5A taken along line 5B-5B (in FIG. 5A), according to an aspect of the present disclosure.

In some examples, the amnion sheet(s) 214 of the cover device 210 are connected to the anvil leg of the surface stapler as shown, for example, in FIGS. 5A and 5B. In other examples, the cover device 210 and amnion sheet(s) 214 can be connected to the staple leg of the cartridge without impacting efficiency of the surgical methods disclosed herein. In other examples, the method can include connecting a first amnion sheet to an inwardly facing surface of the anvil leg and a second amnion sheet to an inwardly facing surface of the staple leg. In this arrangement, multiple amnion sheets 214 can be deployed proximate to a staple line at the surgical site for improving healing, and/or reducing anastomosis leaks.

Once the cover device 210 including the amnion sheet(s) 214 is attached to the leg of the stapler cartridge, at step 312, the method further comprises removing the removable backing 212 attached to a surface of the amnion sheet(s) 214, thereby exposing an inwardly facing surface of the amnion sheet 214 so that the sheet 214 can be attached to tissue of a patient during a stapling surgical procedure.

At step 314, after the removable backing 212 is removed from the amnion sheet(s) 214 exposing the inwardly facing surface of the sheet(s) 214, the method further includes pressing patient tissue at a surgical site between the anvil leg and the staple leg of the surgical stapler and activating the surgical stapler, which causes staples positioned in the staple leg to pass through the amnion sheet 214 and the patient tissue creating a staple line. In this way, the amnion sheet 214 remains fixed to patient tissue at the surgical site preventing the implanted amnion sheet 214 from migrating away from the surgical site and ensuring that the patient tissue is exposed to the amnion sheet 214 to encourage wound healing.

Cartridge for a Surgical Stapler Including an Amnion Sheet or Cover

A cover device 410 or amnion sheet can also be provided as a component of a disposable single-use cartridge 102 for a surgical stapler 124. An exemplary disposable cartridge 102 for a surgical stapler 124, which can be adapted to include a cover device 410 with an amnion sheet, is described in U.S. Pat. No. 7,721,930, entitled "Disposable cartridge with adhesive for use with a stapling device." By integrating the cover device 410 and/or amnion sheet with the disposable cartridge 102, deploying the amnion sheet is made even easier for the surgeon. In particular, the surgeon does not need to position the amnion sheet at the surgical site or even attach the amnion sheet to the stapler. Instead, the surgeon can simply attach the single use cartridge 102 to the stapler 124, as is already done in current practice. Once the cartridge 102 is engaged to the stapler 124, the amnion sheet can be automatically deployed from a leg or portion of the stapler 124 to patient tissue at the surgical site without requiring any extra actions by the surgeon.

Examples of a single-use disposable cartridge 102 including an amnion sheet are shown in FIGS. 5A and 5B. As shown in FIGS. 5A and 5B, the cartridge 102 configured to be connected to the surgical stapler 124 comprises an anvil leg 122 and a staple leg 126 pivotally connected together to grasp patient tissue. The staple leg 126 includes staples 146 positioned in an interior of the staple leg 126 and an inwardly facing surface 148 configured to move towards an inwardly facing surface 150 of the anvil leg 122. The inwardly facing surface 148 of the staple leg 126 includes multiple openings 152 positioned for the staples 146 to pass through the openings 152 to tissue positioned between the inwardly facing surface 150 of the anvil leg 122 and the inwardly facing surface 148 of the staple leg 126.

The cartridge 102 also includes the cover device 410, which comprises an amnion sheet 412, attached to the inwardly facing surface 148, 150 of the anvil leg 122 or the staple leg 126. The sheet 412 can comprise a sleeve or sock that is inserted over the leg 122, 126. In other examples, the sheet 412 can comprise a flat amnion sheet with a backing formed from another material or thread for securing the sheet 412 to the leg 122, 126 of the cartridge 102. In other examples, the sheet 412 may simply be a flat sheet that attaches to a wetted surface of one of the legs 122, 126 without adhesive or any other retaining structure.

As shown in FIGS. 5A and 5B, the cover device 410 comprising the amnion sheet 412 is attached to the anvil leg 122. In other examples, the amnion sheet 412 can be connected to the staple leg 126 or cover devices 410 can be attached to each of the anvil leg 122 and the staple leg 126. The amnion sheet 412 is configured to transfer from the leg 122, 126 of the cartridge 102 to patient tissue positioned between the inwardly facing surface 148, 150 of the anvil leg 122 or the staple leg 126 during a stapling procedure. For example, as previously described, the amnion sheet 412 can be a dried sheet that adheres or transfers to a wetted surface, such as a wetted surface of patient tissue at a surgical site.

As in previous examples, the sheet 412 can include one or more amnion layers. For example, the sheet 412 can be a one ply, two ply, three ply, or four ply amnion sheet 412. Each layer of the amnion sheet 412 can have a thickness of from about 20 μm to 50 μm, preferably about 44 μm. Therefore, a two-play amnion sheet can have a total, dual-layer thickness of from 40 μm to 100 μm, preferably about 88 μm.

The staple leg 126 of the cartridge 102 includes the multiple openings 152 on the inwardly facing surface 148 of the staple leg 126 positioned to provide a specific arrangement of staples 146. The staple leg 126 is generally configured to produce a staple region that is narrow and elongated. The cartridge 102 is configured to project staples 146 through the openings 152 simultaneously so that the staple region is produced by triggering the surgical stapler one time. The multiple openings 152 of the stapler 124 can be arranged in various arrangements of rows and columns. For example, the cartridge 102 can include multiple (e.g., from one to three) columns of openings 152 for staples 146, meaning that the produced staple region is from one to three staples in width. The cartridge 102 can also include multiple (e.g., from three to ten) rows of openings 152, meaning that the produced staple region is from 3 to 10 staples 146 in length. In some examples, the staples 146 within the produced staple region can be equidistantly spaced creating a regular pattern of staples 146 through the staple region. In other examples, staples 146 can be positioned in an offset or alternating pattern in which some staples 146 are farther apart than others in order to provide suitable fixation through the cover device 410 using fewer staples 146.

As previously described, the cartridge 102 can be configured to simultaneously release all staples 146 included in the cavity from the staple leg 126. Once the staples 146 are released from the cartridge 102, the cartridge 102 can be removed from the stapler 124 and discarded. If additional staples are needed for a surgical procedure and/or if another staple line needs to be deployed at another location, a new cartridge 102 can be attached to the stapler 124, and the stapler 124 can be positioned and activated to release the staples 146 from the newly loaded cartridge 102.

In some examples, the cartridge 102 includes a connector 154 connected to or extending from a proximal end of the anvil leg 122 and/or from a proximal end of the staple leg 126. The connector 154 can be configured to engage a corresponding port 156 of a handle of the stapler 124 for connecting the disposable cartridge 102 to other parts of the stapler 124. The connector 154 can be a cylindrical member extending from the proximal end of the cartridge 102. The connector 154 can be configured to be inserted into a corresponding cylindrical port 156 on the handle or body of the surgical stapler 124, thereby removably mounting the cartridge 102 to the stapler 124.

Amnion Sleeve for a Surgical Stapler

FIGS. 7A-7D show an example of a sleeve 710 or sock configured to be attached to a surgical stapler cartridge, such as the cartridge shown in FIGS. 5A and 5B. The sleeve 710 can comprise an open first or proximal end 712 defining an opening 714 (shown in FIG. 7B), a closed second or distal end 716, and longitudinal edges 718 extending between the proximal end 712 and the distal end 716. As shown in FIGS. 7A-7D, the sleeve 710 further comprises a first or top layer or sheet 720 and a second or bottom layer or sheet 722, which are adhered together to form the sleeve 710. For example, portions of the sheets 720, 722 proximate to the closed distal end 716 and longitudinal edges 718 of the sleeve 710 can be adhered together forming an interior sized to receive a leg of a stapler cartridge, such as one of the legs 122, 126 of the cartridge 102 shown in FIGS. 5A and 5B, through the opening 714. As in previous examples, the sheets 720, 722 can comprise amnion. For example, the sheets 720, 722 can comprise a single layer or multi-layer (e.g., two ply, three ply, or four ply) sheet comprising amnion. In some examples, the amnion sheet can be the EvoPatch® implantable patch manufactured by Evologics, LLC of San Antonio, TX, which is a double-layer, chorion-free, dried patch. As shown in FIGS. 7A-7D, one of the sheets 720, 722 of the sleeve 710 can comprise a scored or perforated line 724 extending longitudinally through the sheet 720, 722. The scored or perforated line 724 can be configured to rip or tear due to forces exerted on the sheets 720, 722 by the stapler allowing the sleeve 710 to pop off the cartridge and be deployed on soft tissue proximate to the surgical site.

Dimensions of the sleeve 710 are selected to correspond with dimensions of commonly used or commercially available surgical staplers or cartridges as are known in the art. In some examples, each of the amnion sheets 720, 722 can be about 50 μm to about 100 μm thick or about 88 μm thick, meaning that a total thickness T3 of the sleeve 710 can be about 100 μm thick to about 200 μm thick or about 176 μm thick. A leg of a surgical stapler generally is about 4 cm to about 6 cm in length and about 1.25 cm wide. The sleeve 710 can be sized to fit over or accommodate any conventionally sized surgical stapler leg or cartridge. For example, the sleeve 710 can have a length L3 of about 5 cm to about 7 cm and a width W3 of about 3 cm to about 5 cm. In some examples, the sleeve 710 can be formed from commercially available amnion sheets that are either 5 cm by 7 cm sheets or 4 cm by 6 cm sheets.

Figures 7A, 7B, 7C, 7D:
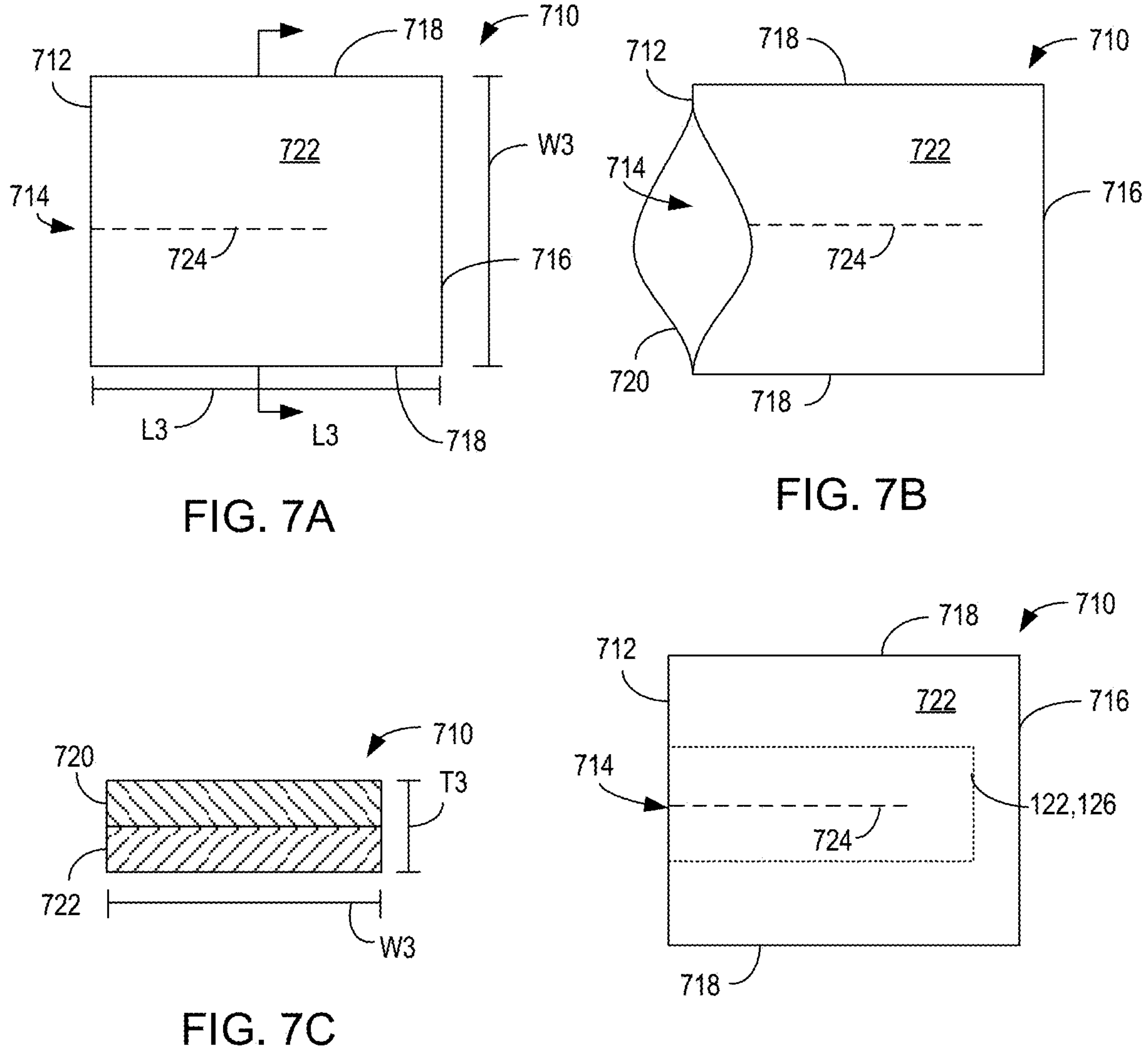
FIG. 7A is a rear view of an example of an implantable sleeve, according to an aspect of the present disclosure.
FIG. 7B is a perspective view of the implantable sleeve of FIG. 7A in an open configuration, according to an aspect of the present disclosure.
FIG. 7C is a cross-sectional view of the implantable sleeve of FIG. 7A taken along line 7C-7C (in FIG. 7A)
FIG. 7D is a schematic drawing showing the implantable sleeve of FIG. 7A inserted over a stapler leg, according to an aspect of the present disclosure.

In order to attach the sleeve 710 to the leg of the surgical stapler or cartridge, the surgeon or another trained professional can position a distal end of the stapler leg 122, 126 proximate to the opening 714 of the sleeve 710. The surgeon or professional may manipulate the sleeve 710 to open the opening 714 as shown in FIG. 7B. The surgeon or professional can then roll the sleeve 710 over the stapler leg so that the sleeve 710 covers all or a substantial portion of both inwardly facing and outwardly facing surface of the stapler leg. Once the sleeve 710 is correctly positioned on the stapler leg 122, 126 as shown in FIG. 7D, the surgeon or another professional can deploy staples at a surgical site. Deploying the staples exerts tension on the sleeve 710 causing the sleeve 710 to rip or tear along the scored or perforated line 724 and to pull away from the surfaces of the stapler leg 122, 126. Also, as in other examples, upon deployment the staples can secure the sleeve 710 to the surgical site over a line of deployed staples aiding in scaling of surgical wounds and promoting tissue healing.

Surgical Methods for Anastomosis

The implantable cover devices 10, 50, 210, 410, 710 of the present disclosure are configured to be fixed to patient tissue during surgical procedures, particularly in forming an anastomosis for tubular structures of the GI tract (e.g., an intestinal anastomosis procedure). Such procedures generally involve forming either an end-to-end anastomosis or a side-to-side anastomosis between the tubular structures (e.g., an intestine or bowel) of the GI tract. The anastomosis techniques described herein can also be transferable to other intra-abdominal procedures involving, for example, intra or extra peritoneal anastomosis, bariatrics, complex appendectomy, small bowel resections, and similar procedures.

Figure 8A:
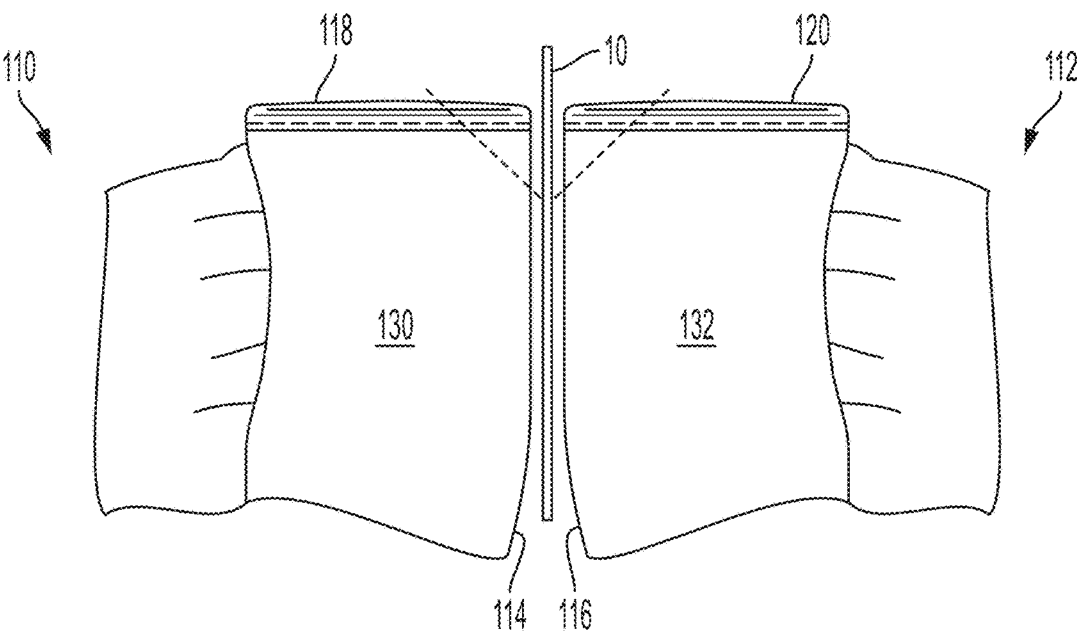
FIGS. 8A-8D are schematic drawings showing steps of a surgical method for forming a side-to-side anastomosis, according to an aspect of the present disclosure.
Figure 8B:
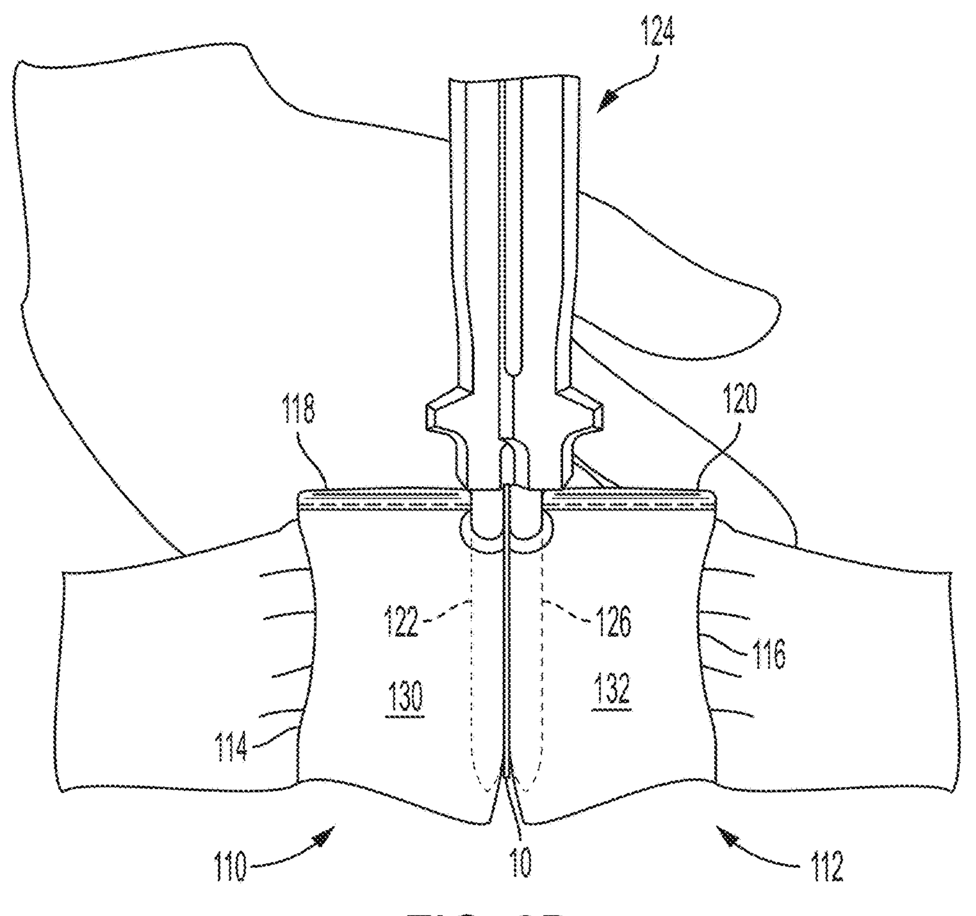

FIGS. 8A-8E are schematic drawings showing steps performed by a surgeon in forming a side-to-side anastomosis using a cover device 210, 410 attached to a leg 122, 126 of a stapler cartridge 102. As described in detail herein, the cover devices 210, 410 are deployed proximate to side surfaces 114, 116 of tubular structures 110, 112 that are being joined together. A second cover device 24 can also be positioned over open ends 118, 120 of the tubular structures 110, 112. After the cover devices 24, 210, 410 are in place, the tubular structures 110, 112 can be connected together by stapling or suturing, such that at least some staples or sutures pass through the cover devices 24, 210, 410. FIG. 9 is a flow chart showing the steps of the side-to-side anastomosis surgical method.

FIGS. 10A-10F are schematic drawings showing steps performed by the surgeon in forming an end-to-end anastomosis, which include deploying or positioning the cover device 10 between open ends 118, 120 of tubular structures 110, 112 of the GI tract prior to connecting the open ends 118, 120 of the tubular structures 110, 112 together. Once the cover device 10 is in place, the tubular structures 110, 112 can be connected together by stapling or suturing, such that at least some staples or sutures pass through the cover device 10. FIG. 11 is a flow chart showing steps performed for the end-to-end anastomosis method.

As shown in FIG. 9, the method for forming the side-to-side anastomosis includes, at step 510, preparing a surgical stapler 124 that includes a cartridge 102 for use in the surgical procedure, such as the anastomosis procedure. As previous described, the cartridge 102 includes the anvil leg 122 comprising an inwardly facing surface 150 and the staple leg 126 with an inwardly facing surface 148 pivotally connected to the anvil leg 122. The staple leg 126 includes multiple staples 146 positioned in an interior of the staple leg 126. The inwardly facing surface 150 of the staple leg 126 is configured to move towards the inwardly facing surface 150 of the anvil leg 122 during use of the stapler 124. The inwardly facing surface 148 of the staple leg 126 can include multiple openings 152 positioned so that the staples 146 can pass through the openings 152 and can be deployed in the patient tissue. As previously described, the cartridge 102 also includes the cover device 210, 410 that includes the one or more amnion sheets 214, 412 attached to the inwardly facing surface 148, 150 of the anvil leg 122 and/or the staple leg 126.

In some examples, the cartridge 102 is provided from a manufacturer or distributor to a medical facility as a pre-assembled cartridge 102 with the amnion sheet 412 integral with the cartridge 102. In other examples, the amnion sheet 214 can be applied to the cartridge 102 by, for example, pressing the amnion sheet 214 of a cover device 210 against one of the legs 122, 126 of the cartridge 102 and then removing a removable backing 212 to expose the inwardly facing surface of the amnion sheet 214, as previously described.

At step 512, once the cartridge 102 and surgical stapler 124 are prepared for use, the method includes positioning patient tissue of a surgical site between the anvil leg 122 and the staple leg 126 of the cartridge 102. For example, the method can include inserting an anvil leg 122 of a surgical stapler 124 through an open end 118 of one of the tubular sections 110, 112 and a staple leg 126 of the surgical stapler 124 through the open end 120 of the other tubular section 112, as shown in FIG. 8B, thereby bringing the amnion sheet 214, 412 into contact with a side surface 114, 116 of one of the tubular sections 110, 112.

Optionally, at step 514, the method can also include positioning another cover device, such as one of the cover devices 10, 50 shown in FIGS. 1A-3B, between the side surface 114 of the first section 110 and the side surface 116 of a second tubular section 112 to provide additional protect and wound healing functionality at the surgical site. The cover device 10 is shown positioned between the tubular sections 110, 112 in FIG. 8A.

At step 516, the method further includes tightening the cartridge 102, which causes the staple leg 126 to move toward the anvil leg 122 and causes the amnion sheet 214, 412 to press against the patient tissue.

At step 518, the method further includes connecting the first tubular section 110 to the second tubular section 112 by activating the stapler 124. Activating the stapler 124 causes staples 146 to pass from the staple portion 126 of the stapler 124, through the side surfaces 114, 116 of the first tubular section 110 and the second tubular section 112, and through the cover device 210, 410 positioned on one of the legs 122, 126 of the cartridge 102. Passing the staples 146 through the cover device 210, 410 fixes the cover device 210, 410 to the tubular sections 110, 112, preventing the cover device 210, 410 from detaching from tissue or migrating during or following completion of the surgical procedure.

At step 520, the method can further include forming an incision through the side surface 114 of the first tubular section 110, the deployed cover devices 10, 210, 410, and the side surface 116 of the second tubular section 112. The incision can be made using a scalpel or similar surgical cutting tool. In some examples, the incision can be formed by a surgical tool manipulated by the robotic-assisted surgery system.

Figure 8C:
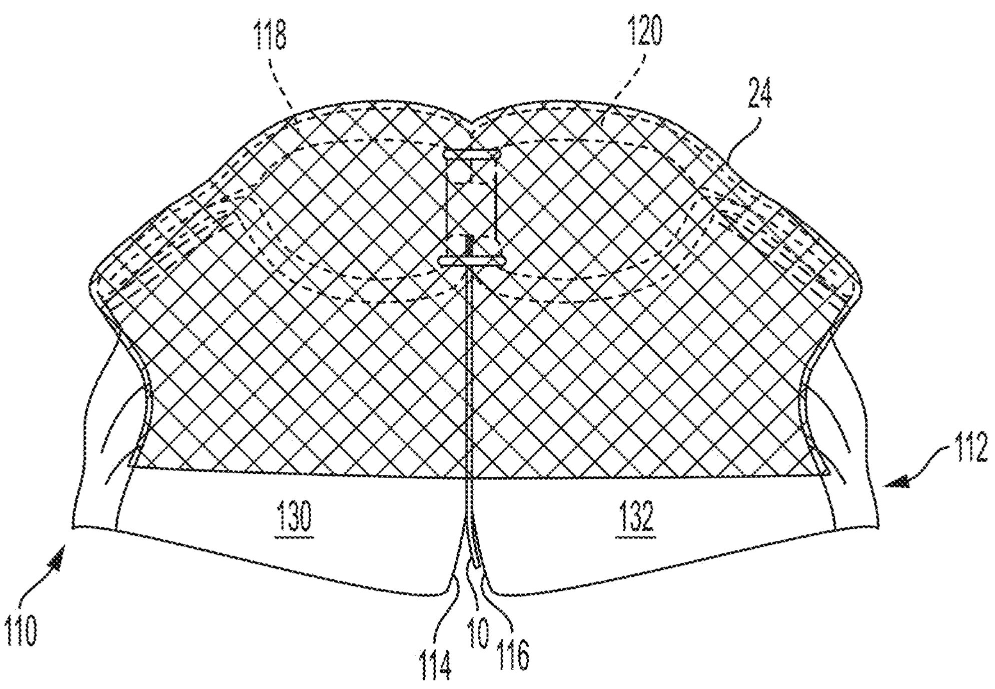
Figure 8D:
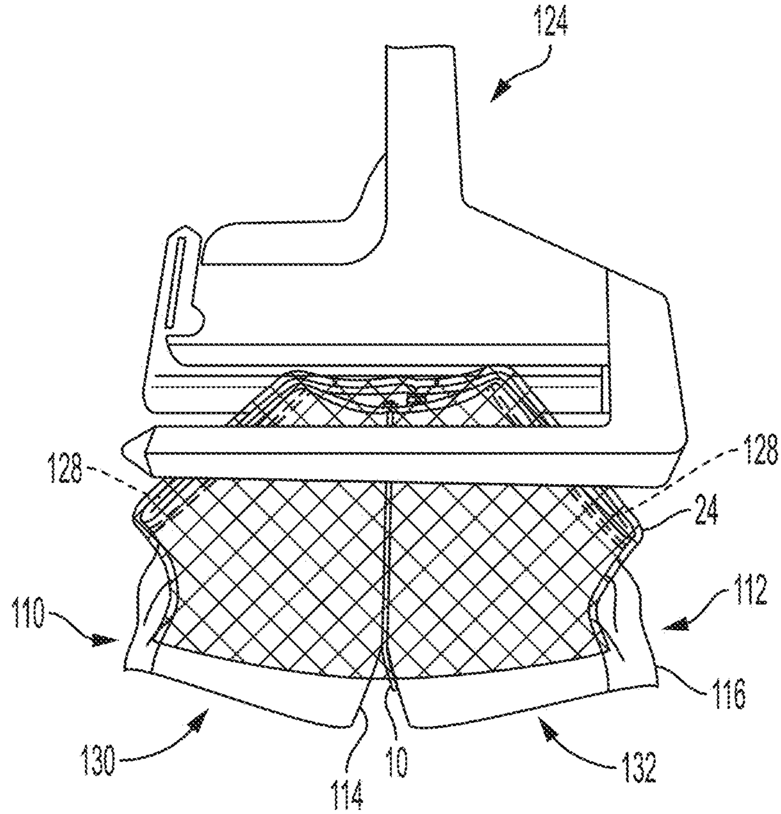
Figure 8E:
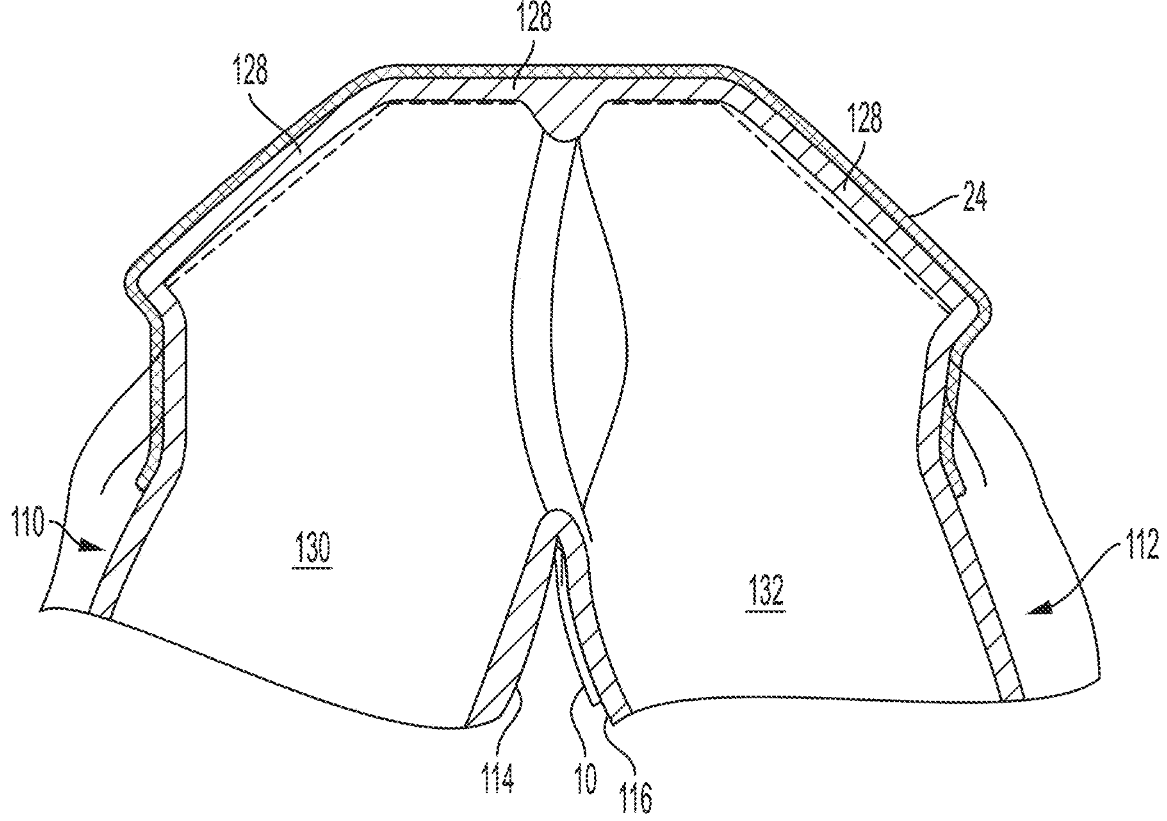
FIG. 8E is a schematic drawing showing tubular sections connected together by a side-to-side anastomosis surgical procedure, according to an aspect of the present disclosure.
Figure 9:
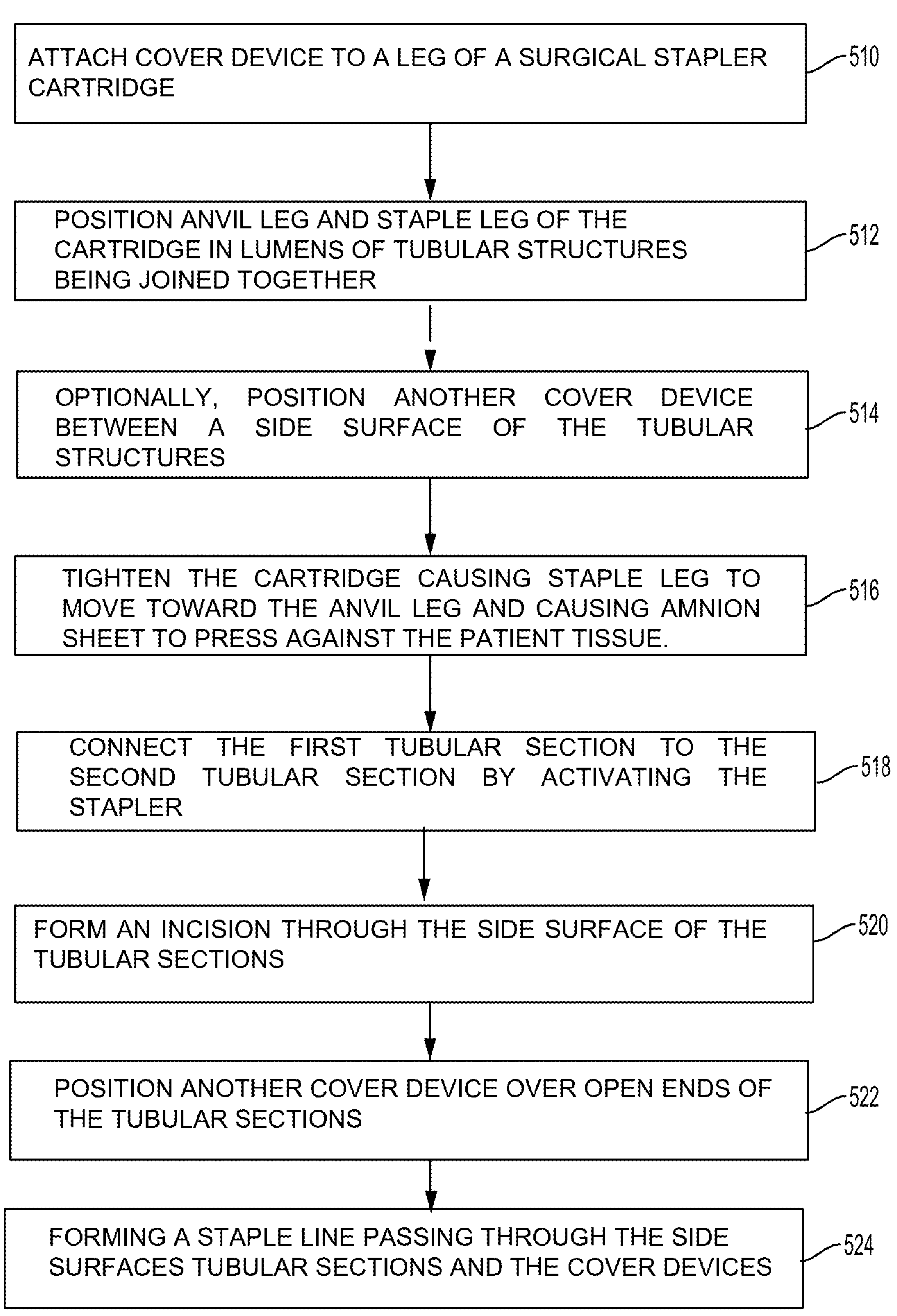
FIG. 9 is a flow chart showing steps of a method for a side-to-side anastomosis surgical procedure, according to an aspect of the disclosure.

At step 522, the method further includes positioning another cover device 24, such as another amnion patch or sheet, over open ends 118, 120 of the tubular sections 110, 112, as shown in FIG. 8C. The second or another cover device 24 can be either a square or rectangle. Further, the annular opening 20, 60 of the cover device 24 can be either centered or offset. At step 524, the method further includes forming a staple line 128 passing through the side surface 114 of the first tubular section 110, the side surface 116 of the second tubular section 112, and the cover device 24. As shown in FIG. 8D, the staple line 128 seals the open ends 118, 120 of the tubular sections 110, 112. Sealing the open ends 118, 120 of the tubular sections 110, 112 forms a continuous lumen extending from a lumen 130 of the first tubular section 110, through the incision, and to a lumen 132 of the second tubular section 112. After forming the staple line 128, any excess tissue above the staple line 128 can be excised. Also, any excess portions of the cover device 24 can be folded over the staple line 128 and/or excised tissue to improve fixation and/or enhance healing of incisions and/or damaged tissue. Desirably, due to the positioning of the cover devices 10, 24, 210, 410, there is no active bleeding through or around the staple line 128. FIG. 7E is a schematic drawing showing the completed side-to-side anastomosis with the continuous lumen extending between the first tubular section 110 and the second tubular section 112.

FIG. 11 is a flow chart showing steps for forming the end-to-end anastomosis, which includes positioning the cover device 10 over an open end 118 of one of the tubular sections 110, 112 being joined together. In the following description, the cover device 10 is described as being positioned proximate to an anvil portion of a surgical stapler. However, when forming the end-to-end anastomosis, the cover device 10 can also be positioned proximate to a stapler portion of the surgical stapler with similar efficiency. FIGS. 10A-10F are schematic drawings showing steps performed during the surgical procedure. The procedure uses a surgical stapler device, particularly an intraluminal circular surgical stapler device 134, comprising a circular stapler portion 136 and anvil portion 138. The circular surgical stapler device 134 is configured to provide staples in a circular pattern in a lumen of a tubular structure. Exemplary circular surgical stapler devices 134, which can be used with the methods disclosed herein are available from Ethicon LLC, Medtronic plc, and others. An exemplary circular stapler device 134, which can be used for the surgical methods disclosed herein, is described in U.S. Pat. No. 9,597,082 entitled "Method and apparatus for sealing end-to-end anastomosis".

With reference to FIG. 11, the method includes, at step 610, positioning a cover device 10, such as a device comprising an amnion sheet 12, between the anvil portion 138 of the surgical stapler device 134 and an open end 118 of a first tubular portion, segment, or section 110 of, for example, the patient's GI tract. The cover device 10 can be a square cover device 10 with an opening 20 in the center of the device 10. The opening 20 of the cover device 10 can be aligned with a lumen 130 of the tubular section 110. In other examples, the cover device 50 can include the offset opening 60 shown in FIG. 3A, which is configured to be offset from the central axis of the lumens 130, 132 of the tubular sections 110, 112. In either case, the cover device 10, 50 can include the markings or guidelines for assisting the surgeon in proper positioning of the amnion sheet and components of a surgical tool, such as the circular surgical stapler. For example, the cover device 10, 50 can include guidelines showing where the stapler should be position and/or where the staple line should be deployed. As shown in FIGS. 2A and 2B, the cover device 10 can also include lines or markings that form a target or dots that help the surgeon to see the cover device 10 when it is attached to the patient tissue. In other examples, a cover device (not shown) can be adhered or attached to the anvil portion 138 of the surgical stapler 134 and configured to transfer from the anvil portion 138 to patient tissue during a surgical procedure. For example, the cover device (not shown) can be attached to the anvil portion 138 immediately prior to performing a surgical procedure by pressing the cover device against the anvil portion 138 and removing any backing materials to expose an inwardly facing surface of an amnion sheet. Alternatively, the anvil portion 138 can be a single-use disposable anvil that is pre-assembled with an amnion sheet, which is deployed to patient tissue during use of the stapler 134.

At step 612 the anvil portion 138 can be advanced, in a direction of arrow A1, through the opening 20 in the cover device 10 and into a lumen of the first tubular section 110. As previously described, the cover device 10 can also be positioned proximate to the stapler portion 134 with similar efficiency.

At step 614, the method can further include cinching the open end 118 of the first tubular section 110 about a stem 140 of the anvil portion 138 by, for example, tightening sutures positioned around the open end 118 of the first tubular section 110. The open end 118 of the first tubular section 110 is shown in this tightened or cinched position in FIG. 9B.

At step 616, the method further includes positioning the stapler portion 136 of the circular surgical stapler 134 in the second tubular section 112, such that a stem 142 of the stapler portion 136 passes through the open end 120 of the second tubular section 112. The stapler portion 136 is shown positioned in the second tubular section 112 in FIG. 10C. As previously described, markings and/or guidelines on the cover device 10, 50 can be provided to assist the surgeon in proper positioning of the surgical stapler.

Figure 10A:
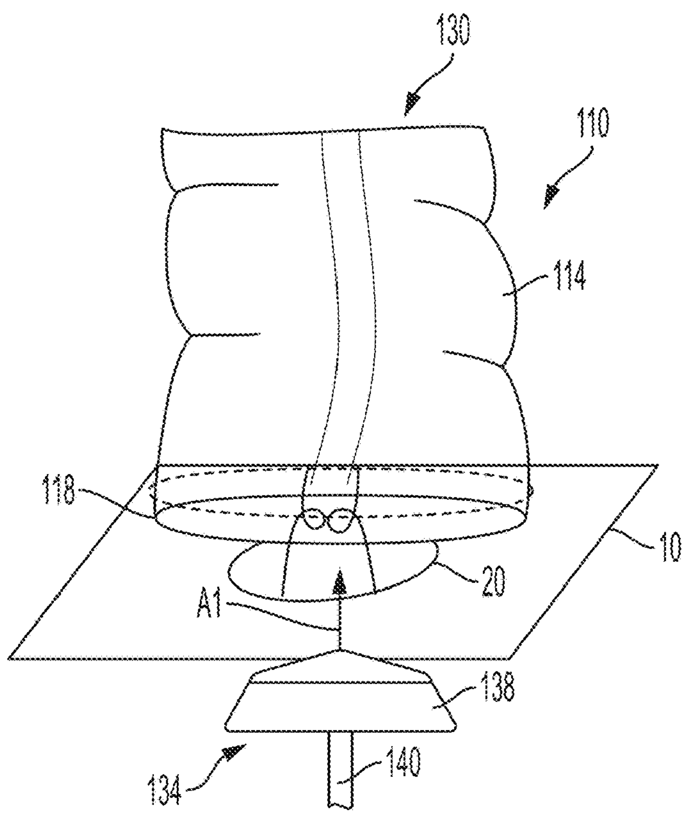
FIGS. 10A-10E are schematic drawings showing steps of a surgical method for forming an end-to-end anastomosis, according to an aspect of the present disclosure.
Figure 10B:
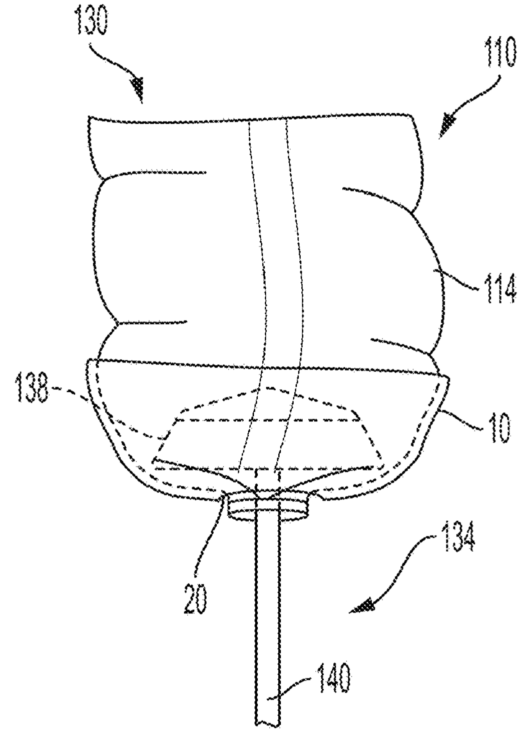
Figures 10C, 10D:
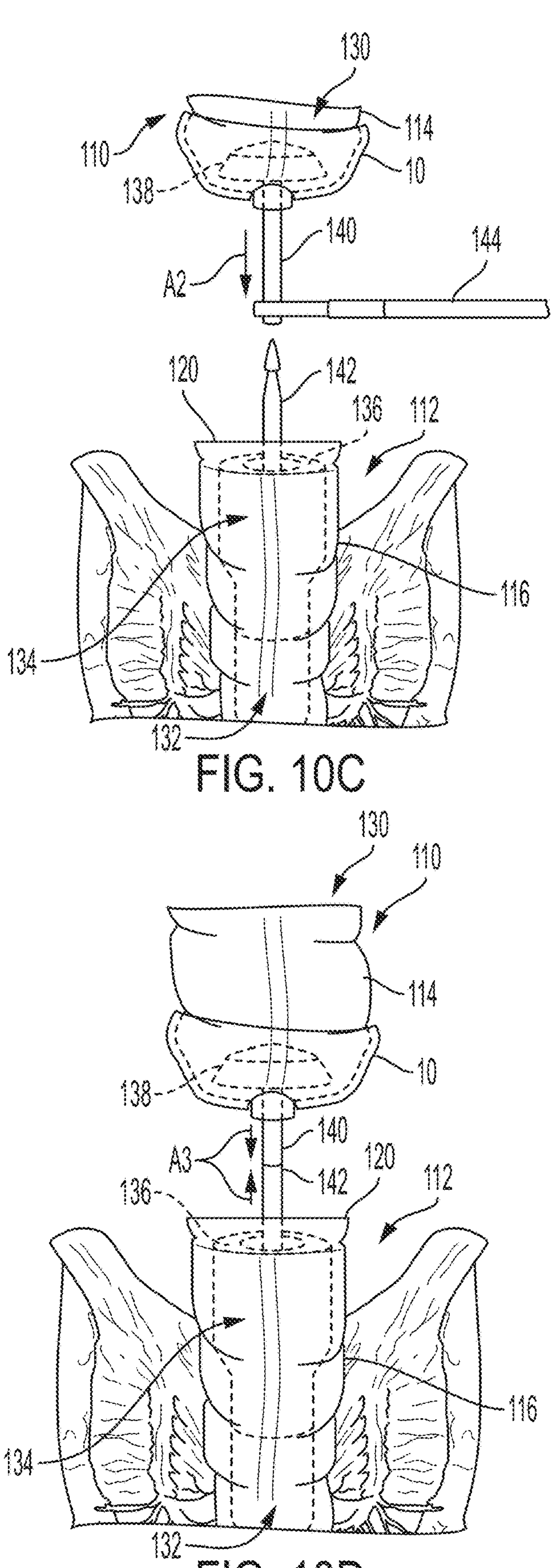
Figure 11:
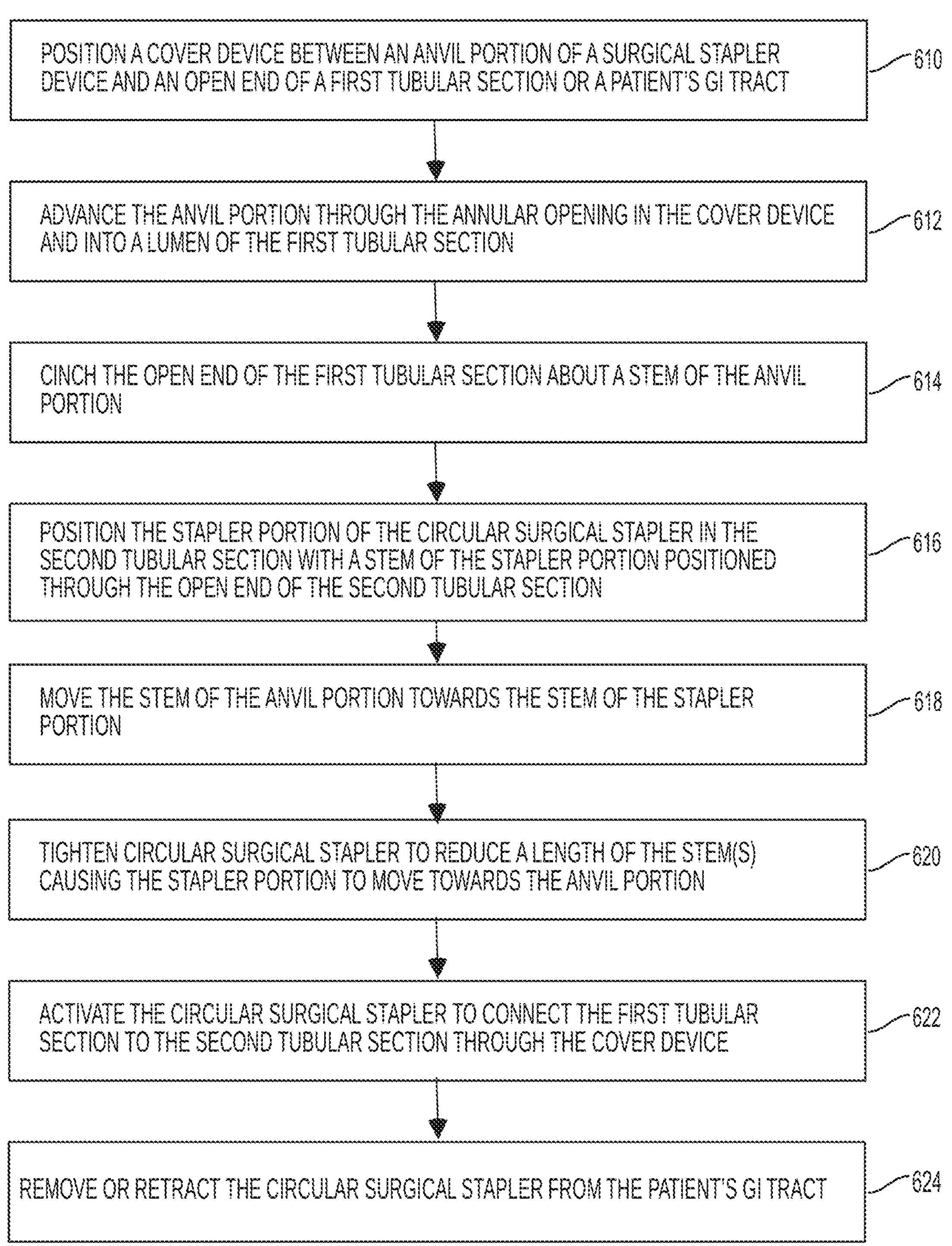
FIG. 11 is a flow chart showing steps of a method for an end-to-end anastomosis surgical procedure, according to an aspect of the present disclosure.

At step 618, as shown in FIG. 10C, the method further includes moving the stem 140 of the anvil portion 138 towards the stem 142 of the stapler portion 136, as shown by arrows A2, using, for example, a clamp 144 or similar tool. The stem 140 of the anvil portion 138 is shown engaged to the stem 142 of the stapler portion 136 in FIG. 10D.

At step 620, once the stems 140, 142 of the anvil portion 138 and the stapler portions 136 are connected together, the method includes tightening the circular surgical stapler 134, which reduces a length of the stem(s) 140, 142 and causes the stapler portion 136 to move towards the anvil portion 138, as shown by arrows A3 in FIG. 10D.

Figure 10E:
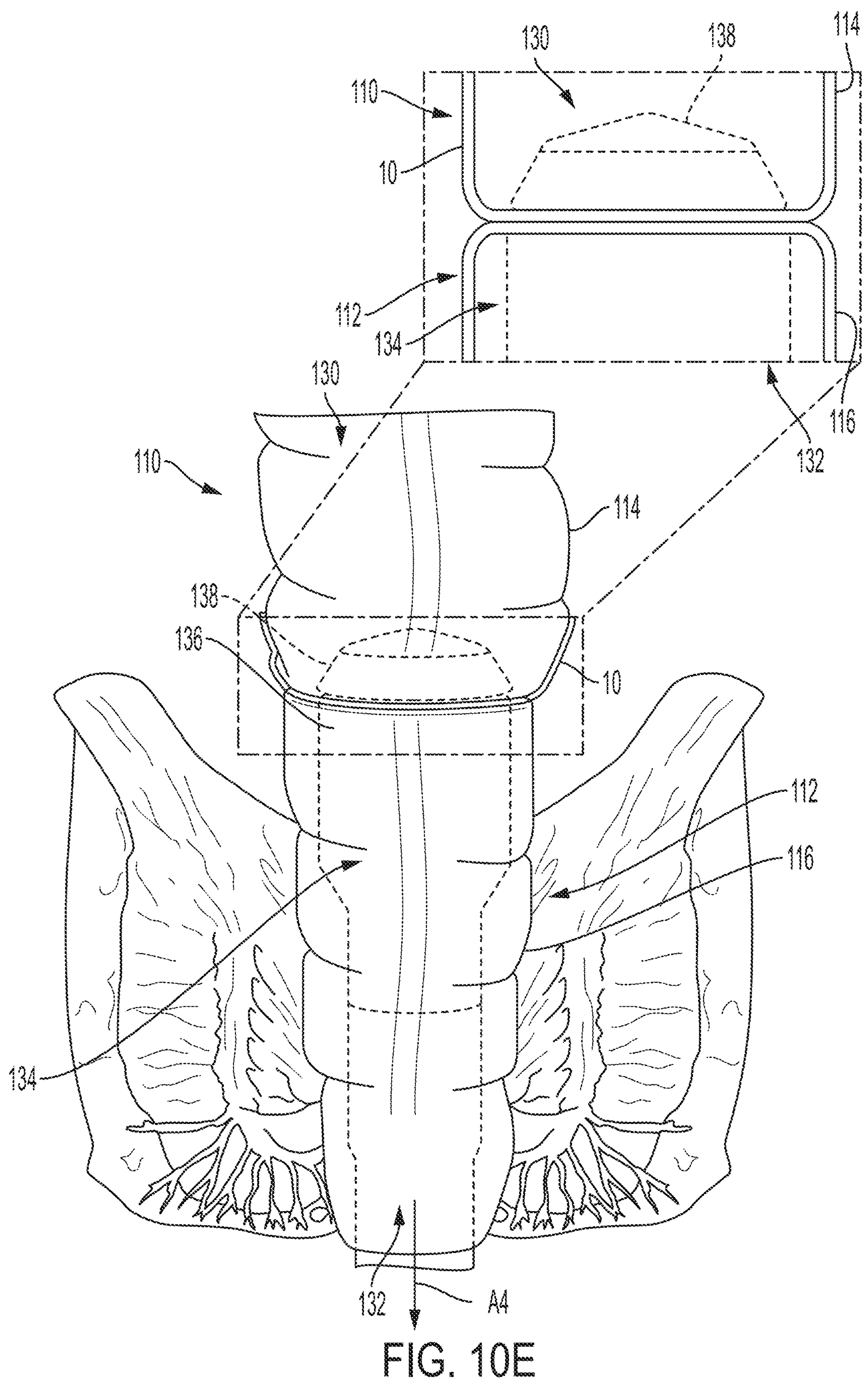

At step 622, once the stapler portion 136 and the anvil portion 138 are fully tightened together as shown in FIG. 10E, the method further includes activating the circular surgical stapler 134 to project staples from the stapler portion 136 through the tubular sections 110, 112 and the cover device 10, thereby connecting the first tubular section 110 to the second tubular section 112. As previously described, the circular surgical stapler 134 is configured to deploy staples in a circular pattern. The deployed staples can extend about the lumens 130, 132 of the first tubular section 110 and/or the second tubular section 112, thereby forming a single continuous lumen passing through an opening or space enclosed by the circle of staples. In other examples, such as when using the cover device 50 with the offset annular opening 60, the deployed staples can be offset from the central axis of the lumen 130, 132. For example, as previously described, deploying the staples offset from the central axis of the lumen 130, 132 may prevent leakage from certain problematic locations near edges or sides of tubular sections 110, 112 being connected together by the end-to-end anastomosis.

Figure 10F:
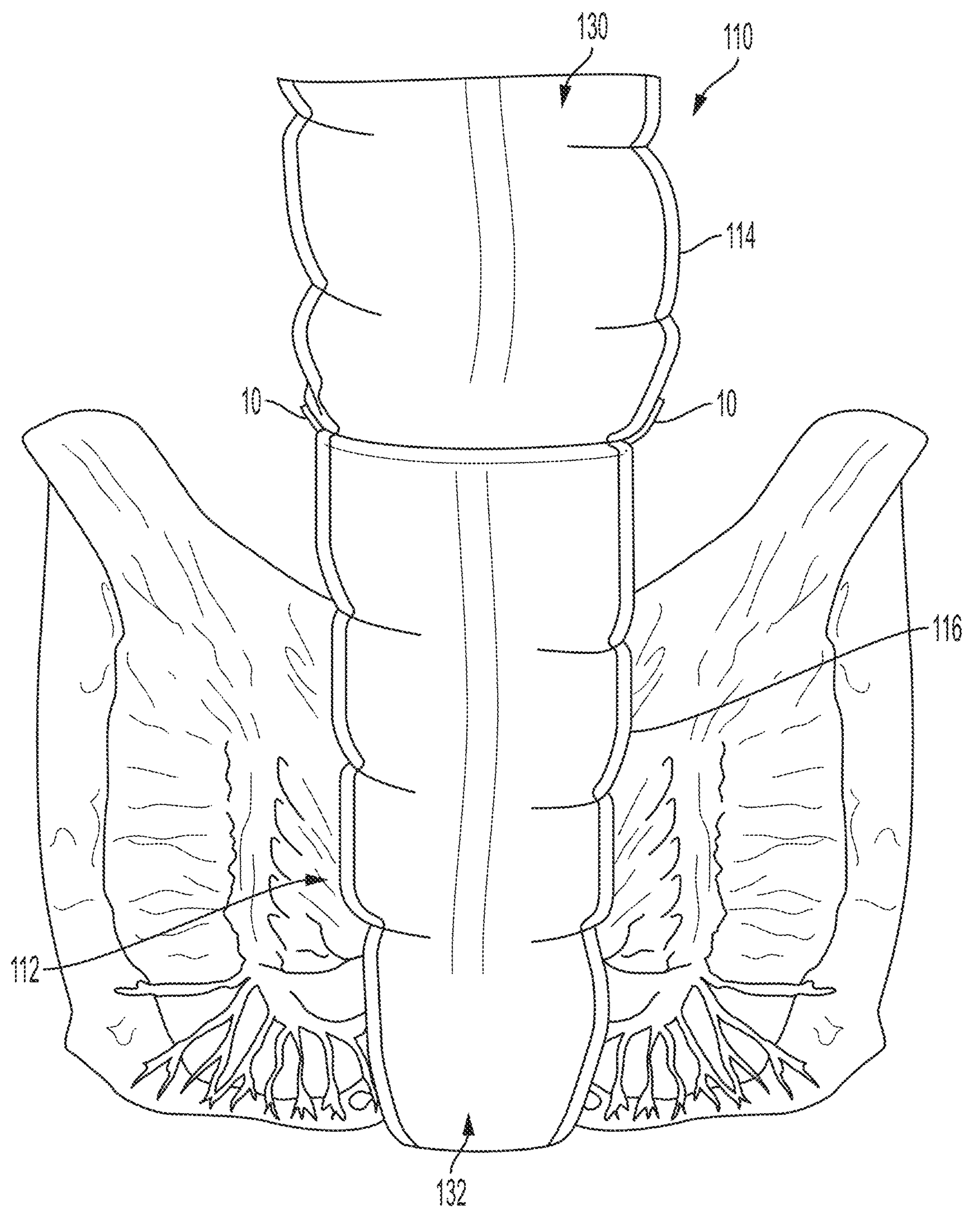
FIG. 10F is a schematic drawing showing tubular sections connected together by a completed end-to-end anastomosis procedure, according to an aspect of the present disclosure.

At step 624, after the staples are deployed through the tubular sections 110, 112 and the cover device 10, the circular surgical stapler 134 can be removed or retracted from the patient's GI tract by moving the anvil portion 138 and stapler portion 136 of the surgical stapler away from the formed anastomosis in a direction of arrow A4 (shown in FIG. 10E). FIG. 10F shows the formed end-to-end anastomosis after removal of the circular surgical stapler 134 from the lumens 130, 132 of the tubular sections 110, 112. As shown in FIG. 10F, once the circular surgical stapler 134 is removed, the lumens 130, 132 form a continuous and unobstructed lumen extending between portions of the GI tract of the patient.

EXAMPLES

In order to show that the cover devices 10 comprising amnion disclosed herein provide an effective seal for reducing leaks in anastomosis procedures, results for surgical procedures performed at a medical facility over a three month period were documented. Specifically, the study included patients who underwent abdominal surgery in which a primary bowel anastomosis was created. Patients were treated either "without amnion" meaning that an amnion sheet or cover device was not positioned over the surgical site or "with amnion" meaning that a cover device or amnion sheet was fixed to the surgical site by a surgical stapler during the procedure. The "without amnion" and "with amnion" groups of patients were compared for anastomotic leak rates, readmissions, re-explorations, and other complications.

Surgical Procedures without Amnion

Eighty-four surgical patients (50 female patients (59.5%) and 34 male patients (40.4%)), underwent an abdominal surgical procedure including a primary intestinal anastomosis creation without use of an amnion sheet or cover device. 72% of these procedures were performed with either a robotic or laparoscopic approach (66% robotic, 6% laparoscopic). 28% of the procedures were either planned open surgical procedures or converted to open procedures. The median patient age at the time of operation was 64.4 years old.

Of the 84 cases studied: 31 patients' pre-operative diagnosis was colon/rectal cancer (36.9%); 32 patients' pre-operative diagnosis was diverticulitis (38%), seven cases (22%) of which were complicated by perforation prior to exploration; seven patients' preoperative diagnosis was defined as "ostomy takedown" (8.3%); seven patients' pre-operative diagnosis was small intestinal obstruction (7.1%); two cases with free perforation prior to arrival at the operating room; one patient with causation secondary to *volvulus*; and one patient with causation secondary to intussusception. Less than 1% of cases had the preoperative diagnosis of small intestinal perforation prior to operation and/or ischemia prior to exploration. All 84 surgical patients studied received close post-operative monitoring with inpatient hospitalization or observation for at least 12 hours post-operation.

Of the patients studied, 10 patients were readmitted (admission prior to 30 days post-discharge) to a hospital facility (12%). Of those patients, the readmitting diagnosis of primary anastomotic failure, defined as bowel content spillage into the abdominal cavity at any time post-procedure, was 5 patients meaning that the overall leak rate was 5.7% (5/84). The overall survival rate of those five patients was 100%. The average hospital stay for those patients with an anastomotic leak was >7 days. 4 of the 5 patients required reoperation. Three patients required 2 additional operations. One patient developed a colo-vaginal fistula and eventually required 3 additional surgeries.

Surgical Procedures with Amnion 79 surgical patients (53 female patients (67%) and 26 male patients (32.9%)), underwent an abdominal surgical procedure including a primary intestinal anastomosis creation. 75% of the surgical procedures were robotic, 24% were either planned open surgical procedures or resulted in open procedures, and 1% were laparoscopically performed. The median patient age at the time of operation was 65.2 years old.

Of the 79 cases studied: 36 patients' pre-operative diagnosis was colon/rectal cancer (45.5%); 20 patients' pre-operative diagnosis was diverticulitis (23.3%), three cases (13%) of which were complicated by perforation prior to exploration; seven patients' pre-operative diagnosis was defined as "ostomy takedown" (8.8%); three patients' pre-operative diagnosis was small intestinal obstruction (3.7%); and one patient with causation secondary to volvulus. All 79 surgical patients studied received close post-operative monitoring with inpatient hospitalization or observation for at least twelve hours post-operation. In each of the 79 procedures, a cover device or amnion sheet, as disclosed herein, was positioned within the surgical site. The cover device 10 was a 6 cm square device. The surgical procedures involved forming a side-to-side anastomosis according to the method of FIGS. 8A-8E and/or an end-to-end anastomosis according to the method of FIGS. 10A-10F. As previously described, during the procedures, staples passed through the cover device 10 to fix the cover device 10 to the surgical site preventing migration of the cover device 10.

No leaks were detected or reported in any of these seventy-nine (79) intestinal anastomoses procedures using the amnion cover device 10, meaning that the leak rate was 0% (0/79).

In view of the results, the present inventor believes that implementation of a cover device comprising amnion in primary intestinal anastomoses shows promising results in decreasing anastomotic leaks and associated complications. In particular, the inventor believes that the study shows that the use of the cover device or amnion sheet appears to significantly reduce the number of anastomotic leaks in intestinal surgery and may therefore reduce the prolonged hospital length of stay and/or the need for readmission, suggesting benefits to both patient outcomes and hospital cost-effectiveness. Follow-on work with cover devices 10, 50 comprising amnion of the present disclosure provided similar results evidencing the effectiveness of the cover device 10, 50 and amnion for improving safety and reducing risks associated with intestinal anastomosis procedures.

What is claimed is:

1. A cartridge configured to be connected to a surgical stapler, comprising an anvil leg comprising an inwardly facing surface;

a staple leg pivotally connected to the anvil leg comprising a plurality of staples positioned in an interior of the staple leg and an inwardly facing surface configured to move towards the inwardly facing surface of the anvil leg, the inwardly facing surface comprising a plurality of openings positioned for the plurality of staples to pass through the plurality of openings to tissue positioned between the inwardly facing surface of the anvil leg and the inwardly facing surface of the staple leg, and a cover device comprising at least one sleeve comprising at least two layers with an inner-most layer of the at least two layers that is configured to contact wetted patient tissue comprising dried and chorion-free amnion attached to the inwardly facing surface of at least one of the anvil leg or the staple leg, the at least one sleeve comprising a proximal end, a distal end, and a curved surface extending therebetween, wherein the at least one sleeve is configured to separate from the inwardly facing surface of at least one of the anvil leg or the staple leg due to forces exerted on the at least one sleeve by the plurality of staples and is configured to adhere and/or remain connected to the wetted patient tissue, such that the at least one sleeve attaches to the tissue positioned between the inwardly facing surface of the anvil leg and the inwardly facing surface of the staple leg with the plurality of staples securing the at least one sleeve to the tissue.

2. The cartridge of claim 1, wherein the at least one sleeve comprises a sheet having a thickness of about 50 μm to about 100 μm.

3. The cartridge of claim 1, wherein the at least one sleeve has a width of about 3 cm to 5 cm and a length of about 5 cm to 7 cm.

4. The cartridge of claim 1, wherein the plurality of openings of the inwardly facing surface of the staple leg is arranged in a substantially linear pattern producing a stapled region that is from 1 to 3 staples in width and from 3 to 10 staples in length.

5. The cartridge of claim 1, wherein the cartridge is configured to simultaneously release the plurality of staples through the plurality of openings upon triggering of the surgical stapler creating at least one staple line through the tissue.

6. The cartridge of claim 1, wherein the cartridge comprises a connector extending from a proximal end of the anvil leg or the staple leg, the connector being configured to engage a corresponding port of a handle of the surgical stapler for connecting the cartridge to the handle.

7. The cartridge of claim 1, wherein the surgical stapler is a gastrointestinal stapler.

8. A cover device configured to be positioned on a leg of a surgical stapler and to transfer from the leg of the surgical stapler to tissue at a surgical site during a stapling procedure, the cover device comprising at least one sleeve comprising at least two layers with an inner-most layer of the at least two layers that is configured to contact wetted patient tissue comprising dried and chorion-free amnion configured to be attached to an inwardly facing surface of the leg of the surgical stapler, the at least one sleeve comprising a proximal end, a distal end, and a curved surface extending therebetween, wherein the at least one sleeve is configured to separate from the inwardly facing surface of the leg of the surgical stapler due to forces exerted on the at least one sleeve by a plurality of staples released by the surgical stapler and is configured to adhere and/or remain connected to the wetted patient tissue, such that the at least one sleeve attaches to the tissue at the surgical site with the plurality of staples securing the at least one sleeve to the tissue.

9. A method for performing a surgical procedure, comprising:

preparing a surgical stapler comprising a cartridge for the surgical procedure, wherein the cartridge comprises:

an anvil leg comprising an inwardly facing surface;

a staple leg pivotally connected to the anvil leg comprising a plurality of staples positioned in an interior of the staple leg and an inwardly facing surface configured to move towards the inwardly facing surface of the anvil leg, the inwardly facing surface comprising a plurality of openings positioned for the plurality of staples to pass through the plurality of openings, and a cover device comprising at least one sleeve comprising at least two layers with an inner-most layer of the at least two layers that is configured to contact wetted patient tissue comprising dried and chorion-free amnion attached to the inwardly facing surface of at least one of the anvil leg or the staple leg, the at least one sleeve comprising a proximal end, a distal end, and a curved surface extending therebetween;

positioning patient tissue of a surgical site between the anvil leg and the staple leg of the cartridge;

tightening the cartridge causing the staple leg to move toward the anvil leg and causing at least a portion of the curved surface of the at least one sleeve to press against the patient tissue, such that the at least one sleeve adheres and/or remains connected to the wetted patient tissue; and activating the surgical stapler causing the plurality of staples to pass from the staple leg through the patient tissue and the at least one sleeve, thereby causing the at least one sleeve to separate from the inwardly facing surface of at least one of the anvil leg or the staple leg due to forces exerted on the at least one sleeve by the plurality of staples and forming at least one staple line in the patient tissue that secures the at least one sleeve to the patient tissue.

10. The cartridge of claim 1, wherein the at least one sleeve further comprises a perforated line extending longitudinally through the at least one sleeve between the proximal end and the distal end of the at least one sleeve, and wherein the forces exerted on the at least one sleeve by the plurality of staples cause the at least one sleeve to separate along the perforated line, thereby separating the at least one sleeve from the inwardly facing surface of at least one of the anvil leg or the staple leg.

11. The cartridge of claim 1, wherein the at least one sleeve is formed from a 5 cm by 7 cm rectangular sheet of amnion or 4 cm by 6 cm rectangular sheet of amnion.

12. The method of claim 9, wherein the at least one sleeve further comprises a perforated line extending longitudinally through the at least one sleeve between the proximal end and the distal end of the at least one sleeve, and wherein the forces exerted on the at least one sleeve by the plurality of staples cause the at least one sleeve to separate along the perforated line, thereby separating the at least one sleeve from the inwardly facing surface of at least one of the anvil leg or the staple leg so that the at least one sleeve is secured to the patient tissue by the plurality of staples.

13. The method of claim 9, wherein activating the surgical stapler releases the plurality of staples producing at least two parallel lines of staples.

14. The method of claim 9, wherein the surgical procedure comprises a side-to-side anastomosis, and wherein positioning patient tissue between the anvil leg and the staple leg of the cartridge comprises inserting the anvil leg and the staple leg through open ends of tubular structures of the gastrointestinal tract of the patient that are to be joined together.

* * * * *